(12) United States Patent
Ekstedt et al.

(10) Patent No.: US 11,395,773 B2
(45) Date of Patent: Jul. 26, 2022

(54) DISPOSABLE HYGIENE ARTICLE WITH IMPROVED FIT

(71) Applicant: Essity Hygiene and Health Aktiebolag, Gothenburg (SE)

(72) Inventors: Sofia Ekstedt, Gothenburg (SE); Josefin Sohl, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/293,145

(22) PCT Filed: Dec. 5, 2018

(86) PCT No.: PCT/SE2018/051255
§ 371 (c)(1),
(2) Date: May 12, 2021

(87) PCT Pub. No.: WO2020/117109
PCT Pub. Date: Jun. 11, 2020

(65) Prior Publication Data
US 2022/0000683 A1     Jan. 6, 2022

(51) Int. Cl.
A61F 13/15      (2006.01)
A61F 13/533    (2006.01)
A61F 13/475    (2006.01)

(52) U.S. Cl.
CPC ........ A61F 13/533 (2013.01); A61F 13/4756 (2013.01)

(58) Field of Classification Search
CPC ........................ A61F 13/533; A61F 13/4756
(Continued)

(56) References Cited

U.S. PATENT DOCUMENTS

| 4,501,586 A | 2/1985 | Holtman |
| 4,765,780 A | 8/1988 | Angstadt |

(Continued)

FOREIGN PATENT DOCUMENTS

| CN | 1496720 A | 5/2004 |
| CN | 1809326 A | 7/2006 |

(Continued)

OTHER PUBLICATIONS

National Intellectual Property Administration (CNIPA) of The People's Republic of China, Notification of the First Office Action, Application No. 201780091799.1, dated Apr. 7, 2020 (15 pages).

(Continued)

Primary Examiner — Jacqueline F Stephens
(74) Attorney, Agent, or Firm — Cantor Colburn LLP

(57) ABSTRACT

The present invention relates to a disposable hygiene article comprising first and second pairs of compression lines in a rear portion of the article. The article has a core with a first region which has its narrowest width (M) in the transverse direction (x) in a front portion or at a location of a transition between the front portion and a crotch portion of the article. The absorbent core in the rear portion comprises the first (L1, R1) and second (L2, R2) pairs of rear compression lines, which extend in a longitudinal direction (y) between respective front and rear endpoints. A longitudinal distance (G1) between the front and rear end points of the first pair of compression lines is less than a longitudinal distance (G2) between the front and rear endpoints of the second pair of compression lines.

28 Claims, 8 Drawing Sheets

(58) Field of Classification Search
USPC .................................. 604/378, 379, 385.101
See application file for complete search history.

(56) References Cited

U.S. PATENT DOCUMENTS

| | | | |
|---|---|---|---|
| 5,149,334 | A | 9/1992 | Lahrman et al. |
| 5,300,054 | A | 4/1994 | Feist et al. |
| 5,312,386 | A * | 5/1994 | Correa ................ A61F 13/4752 604/379 |
| 5,387,208 | A | 2/1995 | Ashton et al. |
| 5,591,149 | A | 1/1997 | Cree et al. |
| 6,486,379 | B1 | 11/2002 | Chen et al. |
| 6,660,902 | B2 | 12/2003 | Widlund et al. |
| 6,986,761 | B1 | 1/2006 | Hines et al. |
| 2003/0130643 | A1 | 7/2003 | Drevik et al. |
| 2005/0004547 | A1 | 1/2005 | Lavash |
| 2005/0182374 | A1 | 8/2005 | Zander et al. |
| 2009/0292268 | A1 | 11/2009 | Bagger-Sjoback et al. |
| 2011/0319851 | A1 | 12/2011 | Kudo et al. |

FOREIGN PATENT DOCUMENTS

| | | |
|---|---|---|
| CN | 101484117 A | 7/2009 |
| CN | 105828761 A | 8/2016 |
| DE | 4004729 A1 | 8/1990 |
| EP | 1035818 A1 | 9/2000 |
| EP | 1253231 A2 | 10/2002 |
| EP | 1493413 A2 | 1/2005 |
| EP | 2092918 A1 | 8/2009 |
| EP | 2103291 B1 | 2/2013 |
| EP | 1402863 B2 | 7/2013 |
| EP | 2934408 A1 | 10/2015 |
| JP | 11113955 A | 4/1999 |
| JP | 2006239162 A | 9/2006 |
| JP | 2011125537 A | 6/2011 |
| JP | 2014195529 A | 10/2014 |
| JP | 2015104645 A | 6/2015 |
| JP | 2015112268 A | 6/2015 |
| JP | 2016049197 A | 4/2016 |
| JP | 2018051110 A | 4/2018 |
| SE | 9401542 L | 11/1995 |
| WO | 9507674 A2 | 3/1995 |
| WO | 9515139 A1 | 6/1995 |
| WO | 2005079722 A1 | 9/2005 |
| WO | 2007008125 A1 | 1/2007 |
| WO | 2008004961 A1 | 1/2008 |
| WO | 2008078805 A1 | 7/2008 |
| WO | 2012057332 A1 | 5/2012 |
| WO | 2012133331 A1 | 10/2012 |
| WO | 2014155757 A1 | 10/2014 |
| WO | 2016031418 A1 | 3/2016 |
| WO | 2017217356 A1 | 12/2017 |
| WO | 2018226131 A1 | 12/2018 |
| WO | 2018226133 A1 | 12/2018 |

OTHER PUBLICATIONS

International Preliminary Report on Patentability for International Application No. PCT/SE2017/050610, dated May 22, 2019, 15 pages.
International Preliminary Report on Patentability for International Application No. PCT/SE2017/050611, dated May 17, 2019, 6 pages.
International Preliminary Report on Patentability for International Application No. PCT/SE2017/050612, dated May 17, 2019, 6 pages.
International Search Report and Written Opinion of the International Searching Authority for International Application No. PCT/SE2017/050610, dated Feb. 13, 2018, 14 pages.
International Search Report and Written Opinion of the International Searching Authority for International Application No. PCT/SE2017/050611, dated Feb. 13, 2018, 12 pages.
International Search Report and Written Opinion of the International Searching Authority for International Application No. PCT/SE2017/050612, dated Feb. 13, 2018, 13 pages.
China National Intellectual Property Administration, Notification of the First Office Action, Application No. 201780091783.0, dated May 8, 2020 (25 pages).
National Intellectual Property Administration (CNIPA) of the People's Republic of China, Notification of the First Office Action, Application No. 201780091784.5, dated Mar. 8, 2021 (26 pages).
Patent-Och Registreringsverket, International Search Report and Written Opinion of the International Searching Authority, International Application No. PCT/SE2018/051252, dated Aug. 28, 2019, 13 pages.
Patent-Och Registreringsverket, International Search Report and Written Opinion of the International Searching Authority, International Application No. PCT/SE2018/051254, dated Aug. 28, 2019, 13 pages.
Patent-Och Registreringsverket, International Search Report and Written Opinion of the International Searching Authority, International Application No. PCT/SE2018/051255, dated Aug. 28, 2019, 13 pages.

* cited by examiner

DISPOSABLE HYGIENE ARTICLE WITH IMPROVED FIT

CROSS REFERENCE TO RELATED APPLICATION

The present application is a U.S. National Stage entry under 35 U.S.C. § 371 of, and claims priority to, International Application No. PCT/SE2018/051255, filed Dec. 5, 2018, the disclosure of which is hereby incorporated herein by reference in its entirety.

FIELD OF THE INVENTION

The present invention relates to disposable hygiene articles, such as sanitary towels, panty liners, incontinence pads or diapers, that are designed so that they adopt a particular form when in use to provide improved fit and security against leakage. The present invention also relates to a method for the manufacture of the disposable hygiene article.

BACKGROUND OF THE INVENTION

Disposable hygiene articles need to have good absorptive properties, comfort and need to provide a sense of leakage security and good fit for a user. Various designs and methods have been employed in hygiene articles so that they could follow the contours of the user's body well and do not move out of place during use.

For example, in the Applicant's own previous International Publication No. WO 2008/004961 A1, an absorbent article with improved fit has been shown. The absorbent article comprises an absorbent core comprising a first region with two legs extending in the longitudinal direction of the article over at least parts of the crotch portion towards separate leg endings in the rear portion. The legs are arranged symmetrically about a longitudinal centre line and a distance between facing sides of the respective legs in the transverse direction varies in the longitudinal direction. A maximum distance is in the crotch portion, located at a position in the longitudinal direction corresponding to a position of a crotch point. The facing sides of the respective legs converge backwards in the longitudinal direction such that the distance is reduced from said maximum distance to a minimum distance in the rear portion. The absorbent core further comprises a second region surrounding said first region and extending between said first region and a circumferential edge of the article. The average density of the absorbent core in the second region is lower than the average density in the first region. By the design promoted, leakage security with good fit and correct, secure placement of the article are obtained. However, despite the efforts to improve the fit of the article, there is still a need to further improve the fit of the article and how the article conforms to the body of the user. Furthermore, there is a need for a simple manufacture method of such products in the existing equipment.

SUMMARY OF THE INVENTION

It has been found that despite prior art solutions for disposable hygiene articles, there is still a need to improve the fit of the article, especially the manner in which the article conforms to the body of the user. There is a need to better control how the article bends and conforms to the body, especially in respect of crotch region and the front part of the article. For comfort and security against leakage, it is important that the article deforms in a predictable manner to fit the anatomy of the user. It is also of importance that existing manufacturing equipment and methods can be used for the manufacture of the articles with minimal modification.

One aspect of the present disclosure is thus to provide a disposable hygiene article with improved fit of the article and an improvement in the manner and consistency with which the article conforms to the body of a user. In particular, the present invention aims to provide an improved fit in the rear portion of the article. Improved fit in the front and crotch portion of the article is also desirable.

A further aspect of the present disclosure is to provide an article with improved comfort for the user, whilst maintaining absorbency that is satisfactory or improving absorbency. The disposable hygiene article may be a sanitary towel, a panty liner, an incontinence pad, absorbent period underwear, or a diaper.

A further aspect of the present disclosure is to provide an article in which absorbed fluid is distributed throughout the article in a manner that minimizes leakage.

Another aspect of the present invention is to provide a disposable hygiene article that can be easily manufactured in existing equipment with minimal modification.

In a first aspect of the present invention, there is provided a disposable hygiene article having a transverse direction, a longitudinal direction and a longitudinal centre line dividing the article into left-hand and right-hand portions. Said article has a front portion, a crotch portion and a rear portion. A liquid-permeable topsheet is provided, as well as a liquid-impermeable backsheet, and an absorbent core arranged between the topsheet and the backsheet.

An outer contour of the absorbent core is defined by mutually symmetric mirror-imaged portions, arranged symmetrically about the longitudinal centerline, and define by symmetrical first and second core edge lines. The absorbent core is also delimited by a core front edge in the front portion and a core rear edge in the rear portion.

In some embodiments, the left and right hand portions of the disposable hygiene article (including the absorbent core, topsheet, backsheet, including any optional fastening or handling features, e.g., wings or handling tabs) is symmetrical about the longitudinal centerline. However, in other embodiments, the absorbent core can be symmetrical about the longitudinal centerline, whilst auxiliary features of the article (e.g., attachment wings or handling tabs) may be provided in an asymmetrical manner. Moreover, by "mutually symmetrical" and "mirror-imaged" it will be understood that each portion may be substantially symmetrical, and that minor or inconsequential deviations from a perfect mirror image fall within the scope of the present invention.

The absorbent core comprises a first region extending in the longitudinal direction of the article from a first region front edge in the front portion over the crotch portion to the rear portion, wherein the outer contour of the first region is defined by mirror-imaged first and second first region edge lines.

In one embodiment, the first region comprises a head part and two leg portions extending symmetrically about the centre line and in a longitudinal direction of the article, starting and diverging from a common leg portion start point in the crotch portion and extending over a portion of the crotch portion towards separate leg portion endings in the rear portion. A distance $a_x$ between facing sides of the respective leg portions in the transverse direction varies in the longitudinal direction, whereby a maximum distance between the facing sides of the respective leg portions in the transverse direction is in the crotch portion, located at a position in the longitudinal direction corresponding to a position of a crotch point, whereby said facing sides of the respective leg portions converge backwards in the longitudinal direction such that said distance $a_x$ is reduced from said maximum distance to a minimum distance $a_2$.

The absorbent core further comprises a second region at least partially surrounded by said first region and extending between said leg portions in the transverse direction and in the length direction from the leg portion start point $a_0$ in the crotch portion to an end point $a_1$ in the rear portion. In this way a second region which conforms to the anatomy of the user can be provided.

According to embodiments of the present invention, the second region has an average density that is lower than the second region. The second region may have an average density which is at least 20%, preferably at least 30% and most preferably at least 50% lower than the average density of the first region. The lower density in the second region of the core can provide different mechanical properties and different absorption properties in a region of the core that comes into close contact with the body of the user.

The absorbent core further comprises two pairs of rear compression lines: a first pair of rear compression lines, in which the lines mutually diverge from each other in a forward direction; and a second pair of rear compression lines mutually diverging from each other in a forward direction. The rear compression lines are positioned in the rear and/or the crotch portion of the article. The first and second pairs of rear compression lines are arranged symmetrically about the centerline. That is, the left compression lines of the first and second pairs of compression lines is a mirror image of the corresponding right compression lines, reflected about the longitudinal centerline.

In at least some embodiments, the first pair of rear compression lines are provided in the crotch portion of the article, wherein the lines mutually diverge in a direction towards the core front edge, wherein the lines have an extension up to the respective first and second first region edge lines and/or the respective first and second core edge lines. Each of the lines can have a diverging angle $\alpha 2$, $\alpha 3$ of from 15-60° in respect of the extension of the centre line.

The first pair of rear compression lines comprises a left compression line left of the longitudinal centre line and a right compression line right of the longitudinal centre line and the second pair of compression lines comprises a left compression line left of the longitudinal centre line and a right compression line right of the longitudinal centre line. The first left compression line extends from a first left front endpoint located at, by or adjacent to a transversally outer left edge of the first leg portion to a rear endpoint located at, by or adjacent to an inner right edge of the first leg portion.

The second left compression line extends from a second left front endpoint located at, by or adjacent to a transversally outer left edge of the first leg portion to a rear endpoint located at, by or adjacent to an inner right edge of the first leg portion. The first right compression line extends from a first right front endpoint located at, by or adjacent to a transversally outer right edge of the second leg portion to a rear endpoint located at or adjacent an inner left edge of the second leg portion. The second right compression line extends from a second right front endpoint located at, by or adjacent to a transversally outer left edge of the second leg portion to a rear endpoint located at, by or adjacent to an inner left edge of the second leg portion.

The compression lines are formed in the first region of the core. By a "front endpoint," it is meant the forward most point of the respective compression line within the first region of the core, i.e., the forwardmost point of the compression line formed in the first region of the core, closest to the front region of the article. By a "rear endpoint," it is meant the rearmost point of the respective compression line formed in the first region of the core, i.e., an end of the compression line formed within the first region of the core, which is closest to the rear edge of the article. The first and second compression lines can comprise a line of compressed material having a higher average density than the first region. Preferably, the compression lines have an average density that is between 30% and 70% higher than the first region.

In embodiments of the present invention, the first pair of rear compression lines is positioned longitudinally forward of the second pair of rear compression lines and are arranged as follows: the front endpoint and the rear endpoint of each of the first pair of compression lines are spaced from each other in a longitudinal direction by a first longitudinal distance G1 and the front endpoint and the rear endpoint of each of the second pair of compression lines are spaced from each other in a longitudinal direction by a second longitudinal distance G2, wherein G2 is larger than G1.

In various embodiments, the second distance G2 is at least 5% longer than the first distance G1, more preferably at least 10% longer, and more preferably at least 20% longer. Preferably, G1 and G2 are between 15 and 90 mm.

In an exemplary embodiment, the first pair of compression lines is configured to allow the hygiene article to conform to a curvature of a user's body in the region of the perineum, and the second pair of compression lines is configured to allow the hygiene article to form a longitudinal ridge in a rear portion of the article to conform to the user's body in between the buttocks.

The first and second rear pairs of compression lines can comprise a continuous region of compression or they can be provided as a series of discrete compression regions arranged to provide a compression line along which the article preferentially folds. Examples of discontinuous compression lines can include a dashed compression line or a compression line comprises a plurality of compression dots.

By providing first and second pairs of compression lines, the second pair having a maximum longitudinal extension that is greater than that of the first pair (particularly in combination with a core comprising first and second core regions as described above), an article may be provided that offers improved fit to the user's anatomy in the rear part of the article. More particularly, the first pair of the compression lines (with the shorter longitudinal distance G1 between the front and rear endpoints) are configured to allow the hygiene article to conform to a curvature of a user's body in the region of the perineum. The second pair of compression lines (with a longer longitudinal distance G2 between the first and second endpoints is configured to allow the hygiene article to form a longitudinal ridge in a rear portion of the article to conform to the user's body in between the buttocks. The improved fit offered by such a configuration may provide increased comfort for the user and improved security against leakage, when compared to conventional sanitary napkins.

A further advantage of the claimed arrangement is that the first and second compression lines do not overlap or meet. This avoids creation of a weak spot at which the materials that form the core, topsheet or backsheet are more likely to tear (during manufacturing or thereafter).

In a first group of embodiments, the front endpoints of the second pair of rear compression lines are located longitudinally forward of the rear end points of the first pair of rear compression lines. That is, the first pair of compression lines overlaps with the second pair of compression lines in the longitudinal direction.

In a second group of embodiments, the front endpoints of the second pair of rear compression lines are located longitudinally behind the rear end points of the first pair of compression lines. That is, the first pair of compression lines and the second pair of compression lines do not overlap in the longitudinal direction.

Whether the first and second pairs of compression lines overlap with each other in a longitudinal direction can be determined based on the dimensions of the article and the core and the distances G1 and G2. In a third group of embodiments, the longitudinal distance between the front endpoints of the second pair of compression lines and the rear endpoints of the first pair of compression lines may be 0. Advantageously, the location of the compression lines and the absolute and relative size of the distances G1 and G2 can be chosen to provide an article that improves the fit of the article against the user's anatomy when in use, as described above. Such modification are applicable to all embodiments of the present invention.

The precise shape and construction of the compression lines can be chosen based on the structure and shape of the disposable absorbent article. Moreover, the shape and construction of the core can be further adapted to optimize fit, absorbency, and fluid distribution. For example, the first region of the core can comprise a head part and two leg portions extending symmetrically about the centre line in a longitudinal direction of the article.

In all embodiments, the front endpoints of the first pair of rear compression lines can be located longitudinally forward of the front endpoints of the second pair of rear compression lines. Alternatively, the front end points of the first and second compression lines can start from approximately the same point on the respective outer edge of the first region of the core. In any of these scenarios, the advantages of the present invention may be realized by the different longitudinal extends of the first and second pairs of compression lines and the different angles at which they approach or intersect the longitudinal centre line.

In any of the above-described embodiments, a distance G3 can be defined in the transverse direction between opposing mirror image-points on the first pair of compression lines, and wherein the G3 increases from a minimum distance $G3_{min}$ between the rear endpoints of the first pair compression lines, and increases continuously in a forward direction to a maximum distance $G3_{max}$ between the front endpoints of the first pair of compression lines. In an exemplary embodiment, G3min is approximately 5 mm, and G3max is 75 mm.

Similarly, a distance G4 can be defined in the transverse direction between opposing mirror-image points on the second pair of compression lines, and wherein the G4 increases from a minimum distance $G4_{min}$ between the rear endpoints of the second pair of compression lines to a maximum distance $G4_{max}$ between front endpoints of the second pair of compression lines. In exemplary embodiments, G4min is approximately 5 mm, and G4max is 80 mm.

The first and second compression lines of the first pair of compression lines and the first and second compression lines of the second pair of compression lines can be straight.

Alternatively, at least one of the first and second pairs of compression lines can be curved. For example, each of the left and right compression lines of one of the first and second pairs of rear compression lines can comprise a curved line, wherein the curved lines curve outwards away from the centre line in a forward direction. The other of the first and second pairs of compression lines can comprise straight lines. Where one of the pairs of compression lines is straight, and the other is curved, preferably, the first pair of compression lines is straight and the second pair of compression lines is curved.

Alternatively, both sets of compression lines can be curved. The first and second left compression lines and the first and second right compression lines can comprise curved lines, wherein for each pair, the lines curve outwards away from the centre line in the forward direction.

When both pairs of compression lines are curved, the left compression lines of the first and second pairs of compression lines can be substantially parallel to each other and the right compression lines can be substantially parallel to each other.

In one embodiment, the first region has its narrowest width in the transverse direction in the front portion of the article, or at the location of a transition between the front portion and the crotch portion.

Optionally, a boundary can be defined between the first region and the second region of the core between the first and second leg portions in the rear portion of the article to form: a first boundary line between an inner edge of the first leg and the second region; and a second boundary line between an inner edge of the second leg and the second region. In this case, and wherein one or both of the first and second pairs of compression lines is curved, and wherein the first boundary line forms a tangential extension of the left curved compression line(s) at the respective rear endpoint, and wherein the second boundary line forms a tangential extension of the right curved compression line(s) at the respective rear end point.

The left and right compression lines of each pair of compression lines can be continuously and increasingly divergent from each other as they extend in the forward direction.

The first and second rear compression lines may be obtained by means of groove compressing the core and optionally the acquisition sheet and/or the topsheet with high pressure compression from the topsheet.

In some embodiments, additional compression lines may be provided in the front region of the article to improve the fit of the article in the front and crotch portion. For example, the article may further comprise left and right front compression lines, said left and right compression lines being symmetrically arranged about the centre line (A). The combination of the front compression lines may provide particular advantages when combined with the first and second rear compression lines described herein because the improved anatomical fit of the article in the front and rear portions of the article allows the crotch region of the article to be maintained in close contact with the user's genitals, thereby improving liquid capture and storage.

Front compression lines can take different forms. For example, the front compression lines can take the form of an X, with first and second arms extending outwardly in a forward direction, and third and fourth arms extending outwardly in a rearward direction. The X can be located with its centre point at or near the narrowest point M of the core.

In further embodiments, the additional front compression lines can comprise a left front compression line that extends from a front endpoint to a rear endpoint via a first turning point and a right front compression lines that extends from a front endpoint to a rear endpoint via a second turning point, with a distance (which is greater than 1 mm) defined between the turning points, at which the front compression lines are a minimum distance from each other.

In such embodiments, the front endpoint of the front left compression line is located at or adjacent to an outer edge region of the first region of the absorbent core left of the longitudinal centre line and forward of a point of narrowest width of the core. The rear endpoint of the front left compression line is located at or adjacent to an outer edge region of the first region of the absorbent core left of the centre line and behind the narrowest width. The first turning point is located left of the centre line and right of the front and rear endpoints in the transverse direction, and between the front and rear end points in the longitudinal direction, wherein the right front compression line extends from a front endpoint to a rear endpoint via a second turning point.

Similarly, the front endpoint of the front right compression line is located at or adjacent to an outer edge region of the first region of the absorbent core right of the longitudinal centre line and forward of the narrowest width. The rear endpoint of the front right compression line is located at or adjacent to an outer edge region of the first region of the absorbent core right of the centre line and behind the narrowest portion. The second turning point is located right of the centre line and left of the front and rear endpoints in the transverse direction, and between the front and rear end points in the longitudinal direction.

The left front compression line and the right front compression line can be spaced from each other by a minimum distance G7 between their respective turning points, and wherein the distance G7 is at least 1 mm in a transverse direction, more preferably at least 2 mm, more preferably between 1 mm and 10 mm, and more preferably between 2 mm and 5 mm.

The second region of the core can comprise a centre region extending symmetrically about the centre line and having a longer extension in the longitudinal direction than in the transverse direction, and a longitudinally and symmetrically about the centre line extending rear section in contact with the centre region, and the centre region and the rear section being limited by the facing sides of the respective leg portions. Thus, the centre region can provide at least a portion of a wetting area of the article.

The maximum width of the centre region can be 10-50 mm and a length can be from 50-110 mm. The minimum width $a_2$ of a rear section limited by the facing sides of the respective leg portions can be 5-30 mm and a length is from 30-110 mm.

The centre region can extend in a thickness direction of the article such that it protrudes outwards from a plane of the first region. It may also optionally comprise a weakening compression line extending along the centre line between a start point and a centre region endpoint. In this way, bending of the centre region longitudinally towards the genitals of the user during use can be further promoted.

The minimum width of a rear section, which is limited by the facing sides of the respective leg portions, can be from 5-30 mm and a length can be from 30-110 mm. The relatively wide forward part of the second region and the relatively narrow rearward part of the second region may improve performance of the article because the wider forward part can provide a comfortable material surface in the region of the article in contact with the vulval vestibule, in the crotch region of the article, whilst the narrower rearward part of the second region between the leg portions is adapted to conform to the region between the buttocks. The wider forward part can be raised and can be slightly curved to sit comfortably against the vulval vestibule.

The first region can have an average density of an absorbent material from 150-220 kg/m$^3$, preferably from 160-210 kg/m$^3$, and the second region can have an average density of an absorbent material from 70-150 kg/m$^3$, preferably from 80-130 kg/m$^3$.

To provide an increased average density in the first region (compared to the second region), said first region can be compressed more than the second region. This can advantageously result in the first region is stiffer than the second region. The second region can cover from 10-50% of a total area of the core.

The higher average density of the absorbent material can be obtained by means of compression and/or providing an embossing pattern to the first region which covers at least portion of the first region, and wherein the second region is free of the embossing pattern. The embossing pattern can comprise individual dots placed in a predetermined pattern. Said first region can be compressed more than the second region, and the first region is stiffer than the second region.

The present invention can be implemented in so-called "daytime" articles, which are optimized for providing protection when the user is in a sitting or standing position, and designed with discretion under clothing in mind. Embodiments of the present invention may be particularly advantageous when implemented in connection with so-called "nighttime" articles, which comprise a greater rear extension when compared to daytime articles. Such articles are dimensioned for improved protection when the user is sleeping, for example when the user is lying down, and may provide additional absorbency to provide protection throughout the night.

To ensure that folding of the article occurs in a well-controlled manner, the compression lines may extend to a point that is at, by or adjacent to the outer edge region of the core. In some embodiments, the outer edge region of the core is an outer edge of the first region of the core. However, in other embodiments, the first region of the core may be at least partially surrounded around its outer edge by a soft outer core region. In such embodiments, the compression lines may extend from the outer edge of the soft outer core, or from the outer edge of the first region of the core.

Although the endpoints may be provided at the outer edge of the first region of the core, the skilled person will understand that the endpoints can be positioned at or adjacent to the outer edge of the first region 12 of the core. An endpoint may be considered adjacent to the outer edge of region of the core, if it is located within 10 mm from the outer edge of the core, more preferably the region defined within 5 mm of the outer edge (measured in the transverse direction x), and more preferably within 2 mm.

In a second aspect of the present invention, there is provided a method for the manufacture of a disposable article. The method comprises the steps of:

feeding a liquid-permeable topsheet material layer, a liquid-impermeable backsheet material layer and an absorbent material layer arranged to be positioned in between the topsheet material layer and the backsheet material layer, forming the first region and second region of the core by compressing the first region more than the second region and/or by embossing an embossing pattern to areas providing the first region in the core, and forming the first pair of rear compression lines and the second pair of rear compression lines, by means of high pressure compression from the topsheet of the core.

The first region can be formed prior to marriage of the backsheet to the absorbent core, topsheet and optional liquid acquisition sheet of the article. In preferred embodiments, the core can be compressed individually before marriage of the core to any of the other materials. In other words, the material of the core can be compressed to produce a varying height and/or density profile before marriage of the core with the topsheet, backsheet, or the optional liquid acquisition material.

The method may also further comprise providing an acquisition material layer between the topsheet material layer and the absorbent material layer.

Further objectives, features and advantages of the disposable hygiene article according to the present disclosure will be apparent from the description below and the appended drawings. Objectives, features and advantages of the method of manufacturing described herein will also be apparent.

BRIEF DESCRIPTION OF THE DRAWINGS

The present invention will now be described with reference to a number of non-limiting illustrative embodiments, in which.

DETAILED DESCRIPTION OF THE INVENTION

The present disposable hygiene article is an absorbent article aimed for personal hygiene and may be, for example, a sanitary towel, a panty liner, an incontinence pad, absorbent period underwear, or a diaper. Such articles are commonly used for acquisition and storage of bodily exudates such as urine, faeces or menstrual fluid. The absorbent article is disposable, which means that it is intended to be used only once and disposed thereafter, rather than being cleaned and re-used. The absorbent article may suitably be a sanitary towel, and the design of the article is particularly suitable for sanitary towels.

Figure 1:
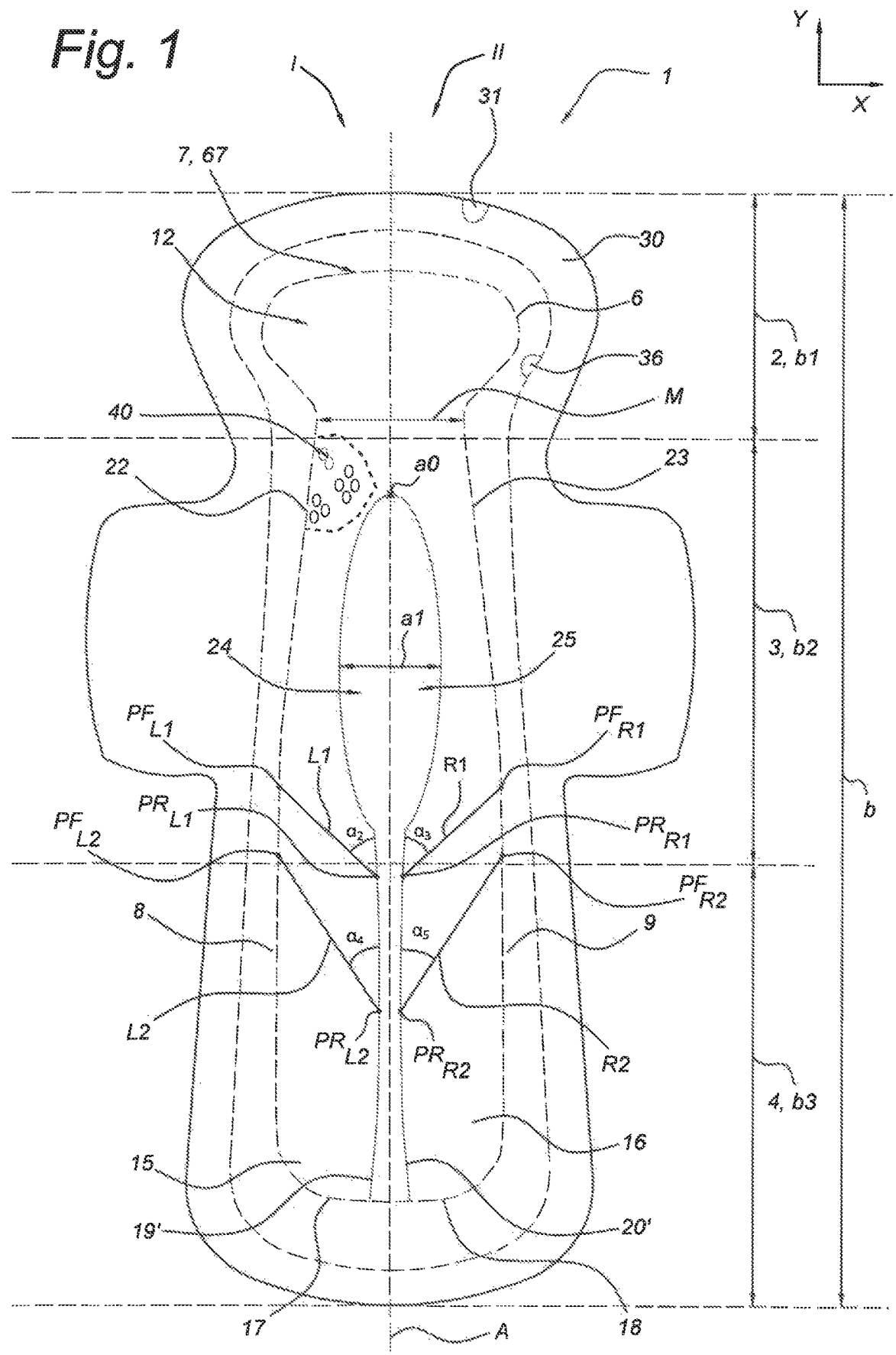
FIG. 1 shows schematically a plan view of an exemplary disposable hygiene article according to the present disclosure, comprising first and second pairs of rear compression lines.

FIG. 1 shows a plan view of an article 1 according to the disclosure. The article 1 shown in FIG. 1 is a sanitary towel. The article 1 has a transverse direction x, a longitudinal direction y and a longitudinal centre line A. The longitudinal centre line A divides the article into left- and right-hand mirror-image halves, I, II, which are symmetrical in shape. By the expression "symmetrical about the longitudinal centre line A," it is herein meant that each point in the article on first longitudinal portion I on a first side of the longitudinal centre line A has a corresponding point in the article on the second longitudinal portion II on the other side of the longitudinal centre line A; the two points being related to each other by reflection in a plane located on the longitudinal centre line A.

The article 1 comprises a front portion 2, a crotch portion 3, and a rear portion 4. The article 1 comprises a liquid-permeable topsheet 30, a liquid-impermeable backsheet 31, and an absorbent core 6 arranged between the topsheet 30 and the backsheet 31. An outer contour of the absorbent core 6 is defined by mirror-imaged first and second core edge lines 8, 9, and the absorbent core 6 is delimited by a core front edge 7 in the front portion 2 and a core rear edge 57 in the rear portion 4.

The absorbent core 6 comprises a first region 12 extending in the longitudinal direction y of the article 1 from the front portion 2 over the crotch portion 3 to the rear portion 4 wherein an outer contour of the first region 12 is defined by mirror-imaged first and second first region edge lines 22, 23 and a first region front edge 67 and a first region rear edge 37.

The core 6 can also comprise a second region 24 (which will be discussed in more detail with reference to FIG. 3), which has a lower density (and thus generally a lower stiffness) than the first region 12 of the core. As shown in FIG. 1, the average density of the first region 12 can be increased (relative to the second region) by applying an embossing pattern 40 to the first region 12.

In the embodiment shown in FIG. 1, the first region 12 of the core 6 and the second region 24 of the core together substantially corresponds to the entire core 6, such that the first region 12 front edge 67 corresponds to the front edge 7 of the core 6, the first region rear edge 37 corresponds to the rear edge 57 of the core 6, and the first region side edges 8,9 corresponds to side edges 22 and 23 of the core 6. However, it will be appreciated that the core 6 can extend outwardly beyond the first region 12 of the core 6. In such embodiments, an additional outer core area is provided, which will be described in more detail with reference to FIG. 4B.

In the embodiment shown in FIG. 1, the outer edge of the first region 12 of the core 6 substantially corresponds to the outer edge of the entire core 6, such that the first region 12 front edge 67 corresponds to the front edge 7 of the core 6, the first region rear edge 37 corresponds to the rear edge 57 of the core 6, and the first region side edges 8, 9 corresponds to side edges 22 and 23 of the core 6. However, it will be appreciated that the first region 12 of the core can extend across only partially across the core 6 such that the boundaries 22, 23, 37, 67 of the first region 12 are spaced apart from (and set within) the boundaries 7, 57, 8, 9 of the core 6. The configuration of the core 6 will be discussed in more detail below with reference to FIGS. 4A and 4B.

As shown in FIG. 1, the first region 12 of the core 6 comprises a narrowest width M (which is narrower than a widest width of the core), as measured in the transverse direction x. The narrowest width M is located in the front portion 2 of the core 6 or at a location of a transition 5 between the front portion 2 of the core and the crotch portion 3 of the core.

As shown in FIG. 1, the first region 12 comprises in the front portion 2 a head portion 13 and two leg portions 15, 16 extending symmetrically about a centre line A and in a longitudinal direction y of the article 1, starting from a leg portion start point $a_0$ in the crotch portion 3 and extending over a portion of the crotch portion 3 towards separate leg portion endings 17, 18 in the rear portion 4. The outer contour of the head portion 13 is defined by two mirror-imaged substantially convex lines in respect to the longitudinal centre line A. The convex lines converge towards the core rear edge 57 and the first region rear edge 37 so as to define a "neck" for the first region 12, i.e., so as to define the narrowest width M in the transverse direction x for the first portion 12 between first and second first region edge lines 22, 23. The narrowest width M may be at the location of a transition 5, which is an area located between the front portion 2 and the crotch portion 3. Alternatively, the narrowest width M is located in the front portion 2 and the transition 5 is located in the longitudinal direction between the narrowest width M and a transversal line crossing the start point $a_0$ for leg portions 15 and 16 of the core. The second region 24 occupies the space between the two leg portions 15, 16.

As shown in FIG. 1, the article 1 comprises two pairs of rear compression lines in the crotch portion 3 and the rear portion 4 of the article 1. The first pair of rear compression lines comprises a first left compression line L1 and a first right compression line R1. The left and right compression lines of the first pair of rear compression lines are symmetrical about the longitudinal centre line A. The second pair of rear compression lines comprises a second left compression line L2 and a second right compression line R2. The first and second compression lines of the second pair of compression lines are symmetrical about the longitudinal centre line A. That is, each of the left compression lines (L1, L2) is a mirror image of the corresponding right compression lines (R1, R2).

Each of the compression lines comprises a rear endpoint and a front endpoint. The first left compression line L1 comprises a front endpoint $PF_{L1}$ and a rear endpoint $PR_{L1}$. The first right compression line R1 comprises a front endpoint $PF_R1$ and a rear endpoint $PR_{R1}$. Similarly, the second left compression line L2 comprises a front endpoint $PF_{L2}$ and a rear endpoint $PR_{L2}$. The second right compression line R2 comprises a front endpoint $PF_{R2}$ and a rear endpoint $PR_{R2}$. The front endpoint of each compression line is positioned forward its rear endpoint.

The front endpoint of each of the compression lines lies at, by or adjacent to an outer edge or an outer edge region of the first region 12 of the core 6. As shown in FIG. 1, the front endpoints $PF_{L1}$, $PF_{L2}$ of the first and second left compression lines L1, L2 are positioned at an outer left edge of the first region 12 of the core 6. The front endpoints $PF_{R1}$, $PF_{R2}$ are positioned at an outer right edge of the first region 12 of the core 6. Although the front endpoints of the first and second pairs of compression lines are shown in FIG. 1 at the outer edge of the first region 12 of the core 6, the skilled person will appreciate that the endpoints can be positioned adjacent to the outer edge of the core, in an outer edge region. In one exemplary embodiment, the outer edge region may be defined as the region within 10 mm from the outer edge of the core, more preferably the region defined within 5 mm of the outer edge of the core (measured in the transverse direction x) from the outer edge.

The rear endpoint of each of the compression lines lies at or adjacent to an inner edge 19, 20 of the leg portions 15, 16. As shown in FIG. 1, the rear endpoints $PR_{L1}$, $PR_{L2}$ of the first and second left compression lines L1, L2 are positioned at an inner right edge 19 of the first leg portion 15, in the rear portion 4 of the article. The rear endpoints $PR_{R1}$, $PR_{R2}$ of the first and second right compression lines R1, R2 are positioned at an inner left edge of the second leg portion 16, again, in the rear portion 4 of the article. Although the rear endpoints of the first and second pairs of compression lines are shown in FIG. 1 at the inner edge 19, 20 of the leg portions 15, 16, the skilled person will appreciate that the endpoints can be positioned adjacent to the inner edge of the core, for example in an inner edge region. In one exemplary embodiment, the inner edge region may be defined as the region within 10 mm from the inner edge of the leg portions, more preferably the region defined within 5 mm of the inner edges of the leg portions 15, 16 (measured in the transverse direction x).

The first pair (L1, R1) and the second pair (L2, R2) of rear compression lines are arranged such that the first pair of compression lines (L1, R1) are positioned forward of the second pair of compression lines (L2, R2), that is towards the front edge 7 of the article 1.

Figure 7:
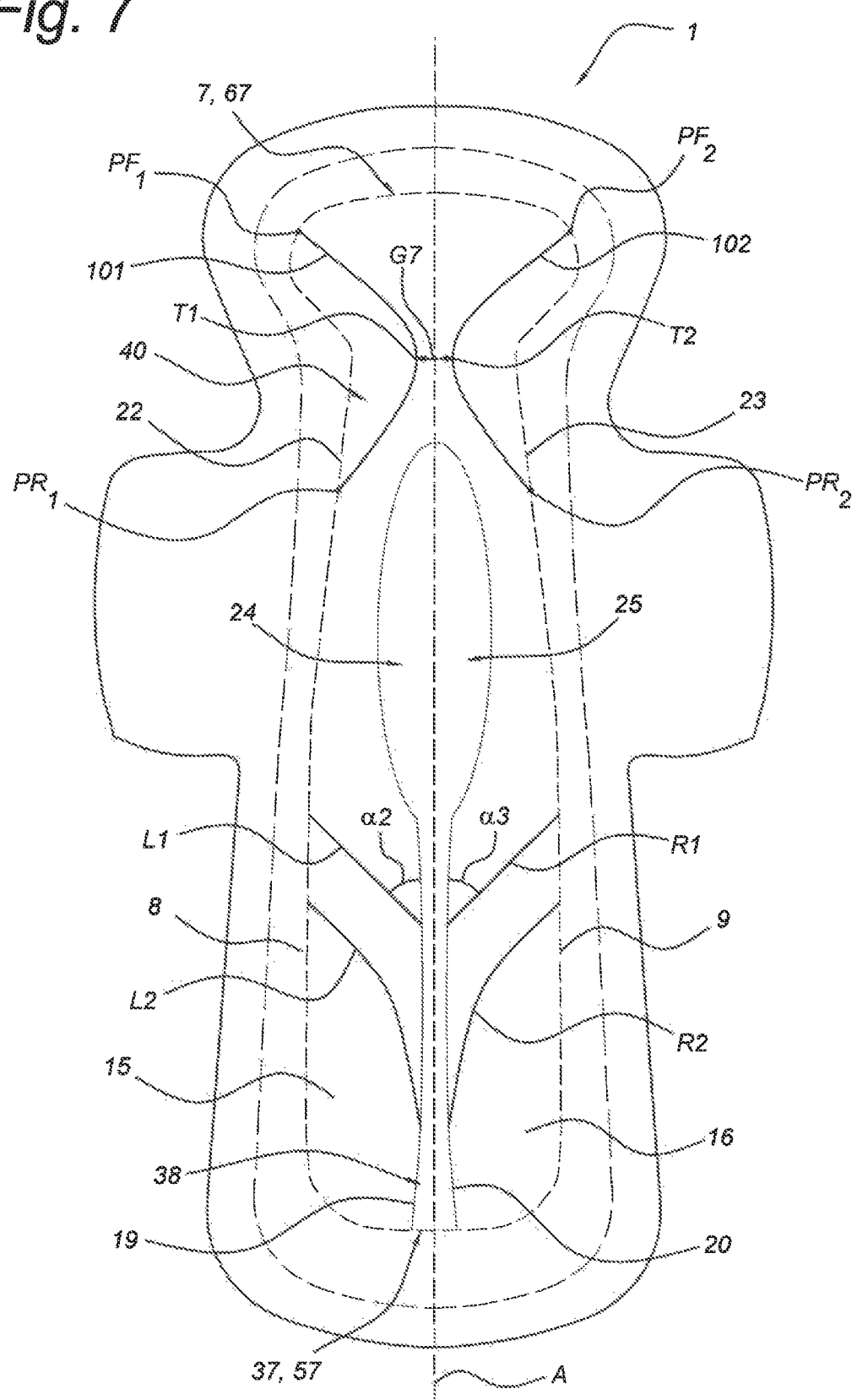
FIG. 7 shows an article according to the disclosure comprising additional front compression lines.

In the embodiments shown in FIG. 1, both pairs of rear compression lines L1, R1, L2, R2 are straight. As illustrated in FIG. 7, the lines have an extension up to the respective first and second first region edge lines and/or the respective first and second core edge lines with a diverging angle $\alpha 2$, $\alpha 3$ of from 15-60° in respect of the extension of the centre line. The second pair of compression lines L2, R2 also have an extension up to the respective first and second region edge lines and/or the respective core edge lines with a diverging angle $\alpha 4$, $\alpha 5$, wherein $\alpha 2=\alpha 3$, $\alpha 4=\alpha 5$, and wherein $\alpha 4>\alpha 5$.

Figure 2:
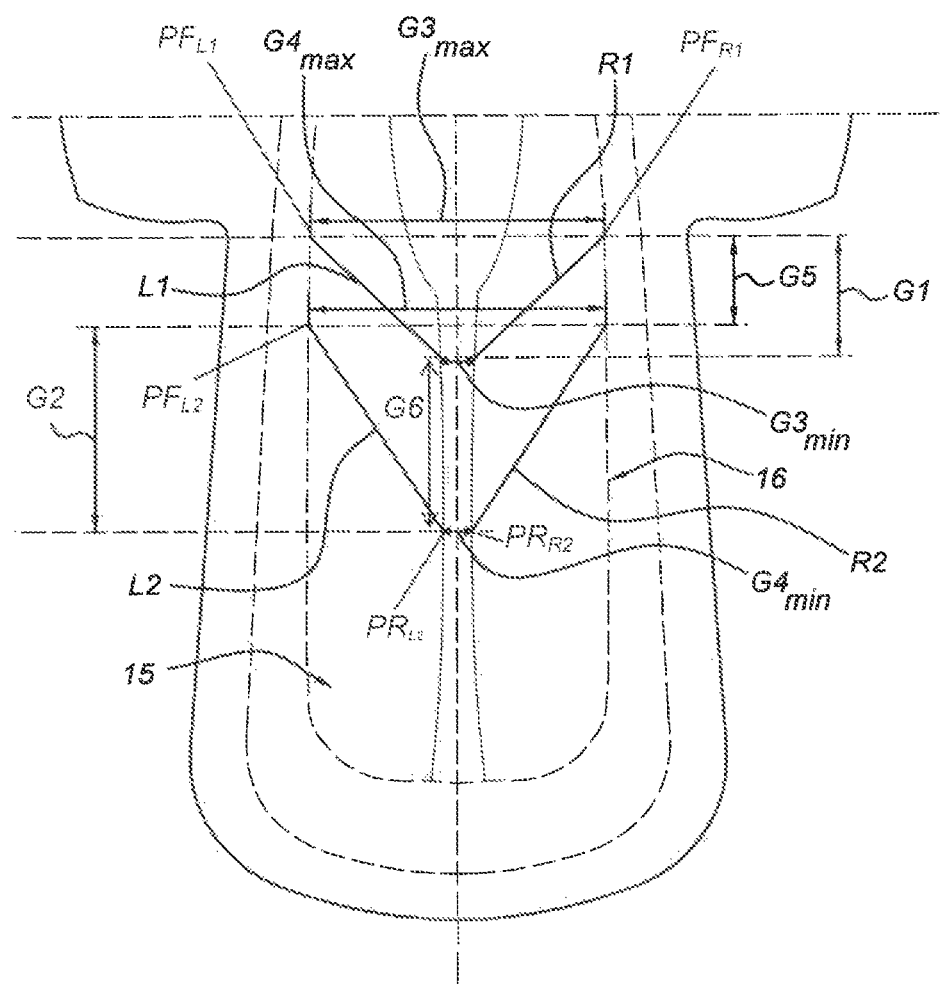
FIG. 2 shows schematically an enlarged view of a rear portion of an article according to a first embodiment of the disclosure.

FIG. 2 shows an enlarged view of the rear portion 4 of the article 1 in FIG. 1. As shown in FIG. 2, a distance G1 is defined between the front $PF_{L1,R1}$ and rear $PR_{L1,R1}$ endpoints ($PR_{L1,R1}$ are clearly shown in FIG. 1) of the first pair of compression lines L1, R1 in the longitudinal direction y. A second distance G2 is defined between the front $PF_{L2,R2}$ ($PF_{R2}$ is clearly shown in FIG. 1) and rear $PR_{L2,R2}$ endpoints of the second pair of compression lines L2, R2 in the longitudinal direction y. The second distance G2 is larger than the first distance G1. In preferred embodiments, the second distance G2 is at least 5% longer than the first distance G1, more preferably at least 10% longer, and more preferably at least 20% longer.

The difference between the longitudinal distances G1 and G2 provides two pairs of compression lines that provide controlled folding of the article 1 at different angles with respect to the centre line A that allows the article to better conform to the user's anatomy. As will become apparent from the present disclosure, the first pair of rear compression lines (L1, R1)—with a relatively short longitudinal distance G1 between the front and rear endpoints—are configured to allow the hygiene article to conform to a curvature of a user's body in the region of the perineum. The second pair of rear compression lines—with a longer longitudinal distance G2 between the front and rear endpoints—is configured to allow the hygiene article to form a longitudinal ridge in a rear portion of the article to conform to the user's body in between the buttocks. This improved the comfort of the article for the user and provides additional security against leakage due to the closer fit against the user's body, in the genital region, where fluid is to be quickly captured and absorbed.

In other words, the difference between the distances G1 and G2 can provide first and second pairs of compression lines having different pitch or gradient with respect to the centre line A. The first pair of compression lines provide a relative shallow outward incline away from the centre line A towards the outer edges of the first region 12 of the core 6. Whereas, the second pair of compression lines provide a relatively steep incline away from the centre line A towards the outer edge of the core. The shallow incline of the first pair of compression lines provides controlled folding in the region of the perineum to allow the article to fold upwardly around the curve of the buttocks, in a rearward direction. The steeper incline of the second pair of compression lines provides controlled folding in the region between the buttocks, allowing the rearmost portion of the article 1 to bend in a longitudinal direction so that the rear part of the article can better confirm to the crease between the user's buttocks.

Although the endpoints of the compression lines are shown in FIGS. 1 and 2 at the outer edge of the first region 12 of the core 6, the skilled person will appreciate that the endpoints can be positioned at or adjacent to the outer edge of the first region 12 of the core 6. An endpoint may be considered adjacent to the first region 12 of the core 6 if it is located within 10 mm from the outer edge of the core, more preferably the region defined within 5 mm of the outer edge of the core (measured in the transverse direction x), and more preferably within 2 mm.

In an exemplary embodiment, each of the first (L1, R1) and second (L2, R2) pairs of compression lines is increasingly and continuously divergent, as they extend in the forward direction. That is, for each pair of compression lines, the distance between the first and second compression lines in the transverse direction x increases from a minimum distance at the rear end points, to a maximum distance at the front points. In other words, and as shown in FIG. 2, a distance G3 is defined in the transverse direction x between opposing mirror image-points on the first pair of compression lines L1, R1 and G3 increases from a minimum distance $G3_{min}$ between the rear endpoints of the first pair compression lines L1, R1, increasing continuously in a forward direction to a maximum distance $G3_{max}$ between the front endpoints of the first pair of compression lines L1, R1.

The second pair of compression lines is also divergent in the forward direction. As shown in FIG. 2, a distance G4 is defined in the transverse direction x between opposing mirror-image points on the second pair of compression lines L2, R2, and wherein the G4 increases from a minimum distance $G4_{min}$ between the rear endpoints of the second pair of compression lines L2, R2 to a maximum distance $G4_{max}$ between front endpoints of the second pair of compression lines L2, R2. Each of G3min and G4min are preferably at least 1 mm, more preferably at least 2 mm, but preferably less than 20 mm, more preferably less than 15 mm, and more preferably less than 10 mm.

Figure 5:
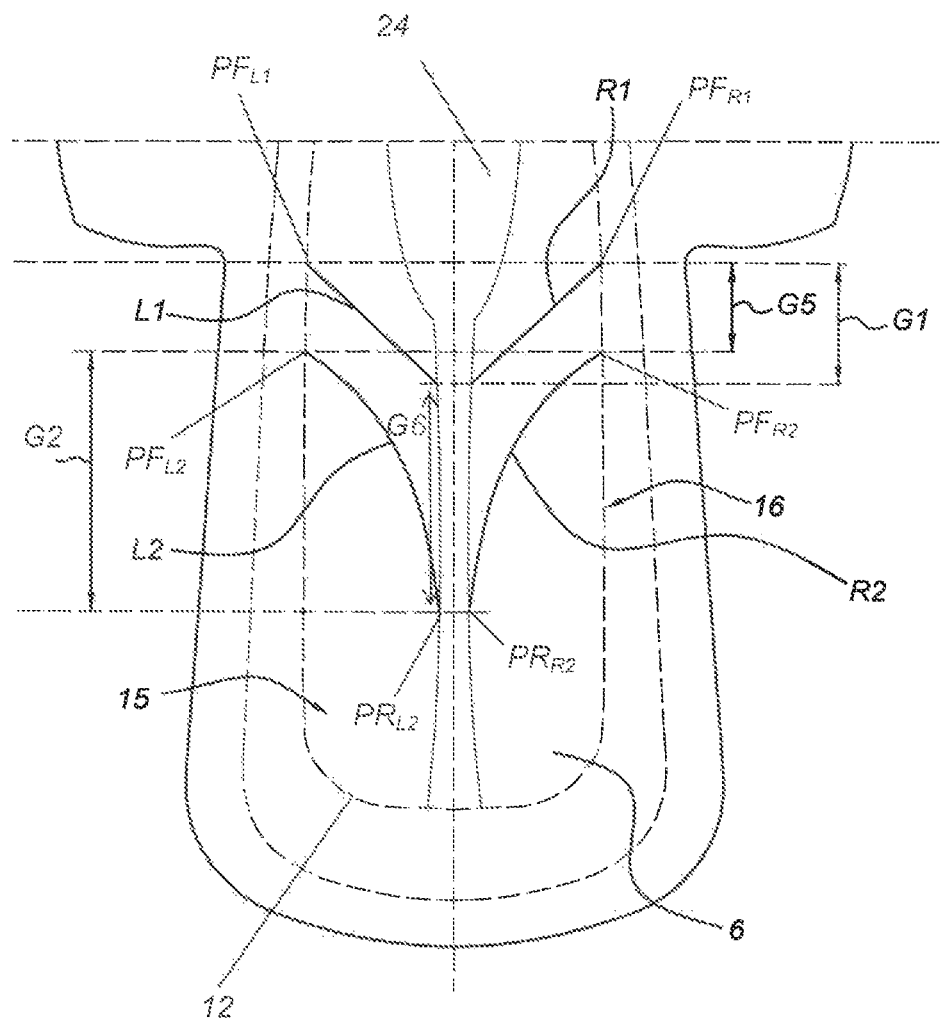
FIG. 5 shows schematically a plan view of a rear portion of an article according to a second embodiment of the disclosure.

Further distances G5 and G6 can also be defined in the longitudinal distance y between the front endpoints of each of the first and second pair of the compression lines and the rear endpoints of the first and second compression lines. As shown in FIG. 5, a longitudinal distance between the front endpoints of the right compression lines R1, R2 is defined as G5. A longitudinal distance between the rear end points of the right compression lines R1, R2 is G6. Because the left and right compression lines are symmetrical about longitudinal centre line A, the distance between the respective end points is the same for the left compression lines L1, L2 as for the right compression lines R1, R2. In various embodiments, the distance G6 is greater than G5. In other words, the distance between the first and second left compression lines increases as the compression lines L1, L2 extend from the front endpoint to the rear end point. Although this arrangement is preferred, such an arrangement in which G6>G5 is not essential. In preferred embodiments, G5 is at least 5% smaller than G6, more preferably at least 50% smaller than G6. In some examples, G5=10-70 mm and G6=10-90 mm As will be described in more detail with reference to FIGS. 5 and 6, the first and second pairs of rear compression lines can take several forms, whilst providing the above described advantages.

The advantages of the present invention can be achieved with minimal disruption to or modification of known manufacturing techniques. In a production method suitable for manufacturing articles according to the present invention, a liquid-permeable topsheet material layer 30, a liquid-impermeable backsheet material layer, and an absorbent material layer are fed into the manufacturing equipment. The core is arranged to be positioned in between the topsheet material layer 30 and the backsheet material layer. An optional acquisition material layer is arranged to be positioned between the topsheet material layer 30 and the absorbent material layer. Before, during, or after the marriage of the above-described materials to form an absorbent article, the compression lines 101, 102 are compressed by means of high pressure compression from the topsheet or the backsheet side of the core. In various embodiments, the compression lines are formed prior to marriage of the backsheet to the absorbent core, topsheet, and the optional liquid acquisition sheet 36 of the article. In yet another embodiment, the core can be compressed individually before marriage of the core to any of the other materials. In other words, the material of the core can be compressed to produce a varying height and/or density profile before marriage of the core with the topsheet, backsheet, or the optional liquid acquisition material.

Figure 3:
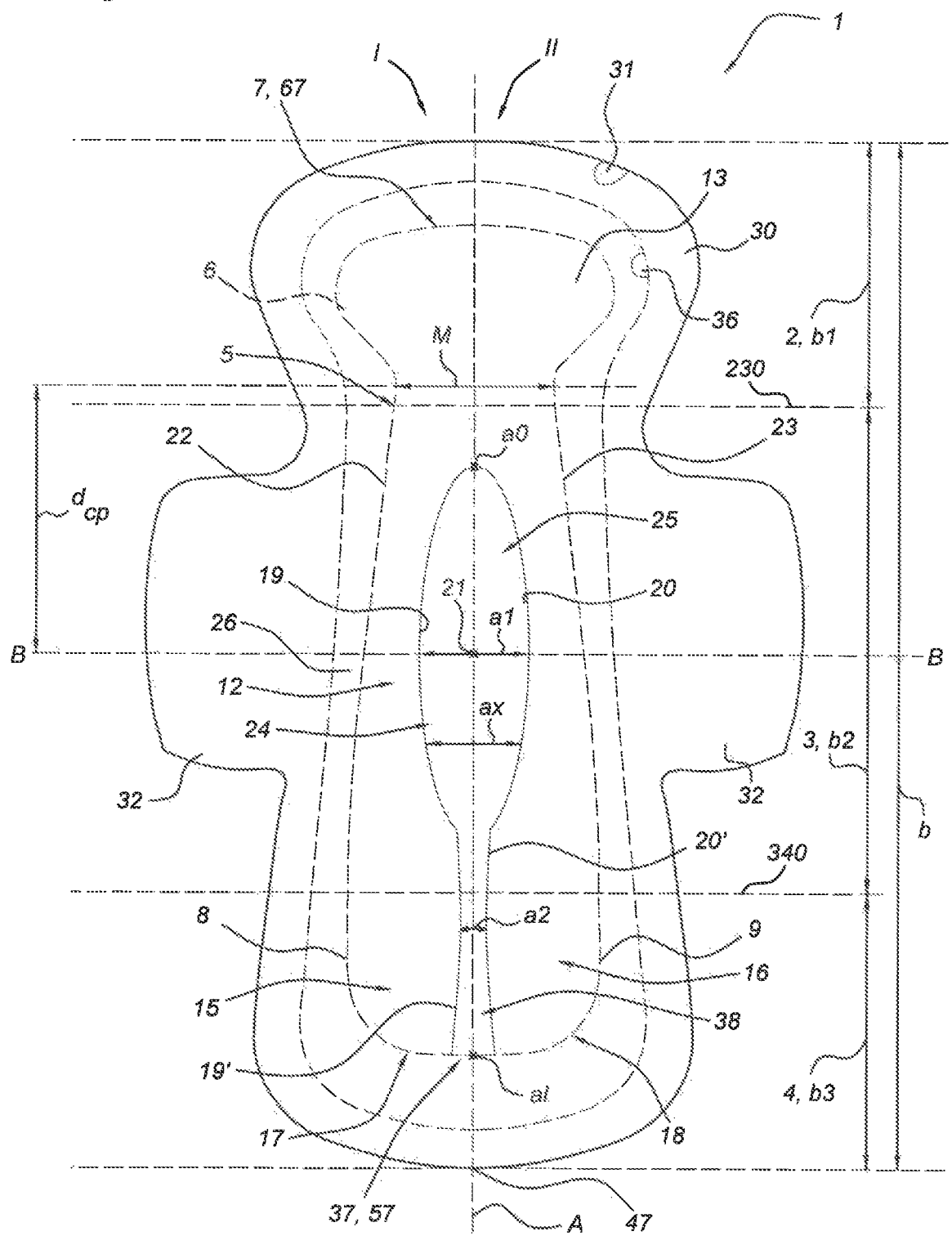
FIG. 3 shows schematically a plan view of an exemplary disposable hygiene article according to the present disclosure.

Turning now to FIG. 3, an exemplary embodiment of the present invention will now be described in which the core 6 comprises a first region 12 and a second region 24. For clarity, the rear compression lines L1, R1, L2, R2 are omitted from the schematic drawing shown in FIG. 3, which serves to provide further details of the absorbent core into which the first and second pairs of rear compression lines can be incorporated. However, the compression lines L1, R1, L2, R2 shown in FIGS. 1 and 2 (and FIGS. 4-7) may be superimposed onto the article shown in FIG. 3.

As shown in FIG. 3, the disposable hygiene article 1 comprises a transverse direction x, a longitudinal direction y and a longitudinal centre line A as indicated. The article can be divided into a first and second mirror imaged longitudinal portions I and II, wherein the longitudinal portions are symmetrical in shape. By the expression "symmetrical about the longitudinal centre line A," it is herein meant that each point in the article on first longitudinal portion I on a first side of the longitudinal centre line A has a corresponding point in the article on the second longitudinal portion II on the other side of the longitudinal centre line A; the two points being related to each other by reflection in a plane located on the longitudinal centre line A. For example, a part of the first region 12 located on the left side of the longitudinal centre line A is therefore the mirror image of the part of the first region 12 located on the other side of the longitudinal centre line A. This is clearly shown in FIG. 2.

The total length of the article 1 in the longitudinal direction is length b, which is the sum of a length b1 of a front portion 2, a length b2 of a crotch portion 3 and a length b3 of a rear portion 4, and sums up to 100% length of the article. The front portion 2, a crotch portion 3 and a rear portion 4 are arranged in the article's longitudinal direction as well as a transition 5 between the front portion 2 and the crotch portion 3. A first Imaginary line 230 extends in a transverse direction to separate the front portion 2 from the crotch portion 3, and a second imaginary line 340 extends in the transverse direction to separate the crotch portion 3 from the rear portion 4. The article comprises an absorbent core 6.

The disposable hygiene articles depicted in FIG. 3 is a so-called "daytime" article, optimized for providing protection when the user is in a sitting or standing position, and designed with discretion under clothing in mind. However, the skilled person will appreciate that the present invention may also be implemented in a so-called "nighttime" article, which comprises a greater rear extension (rear section 4) when compared to daytime article (see, e.g., FIG. 1). Such articles can be dimensioned for improved protection when the user is sleeping, for example when the user is lying down, and may provide additional absorbency to provide protection throughout the night, when compared to daytime products.

The skilled person will appreciate that although the present invention is suitable for use in a wide range of articles comprising different rear extensions, the advantages of the present invention may be particularly beneficial in articles with a longer rear extension.

In use, the front portion 2 of the article 1 is intended to cover at least partly the pubic region of a female wearer. The front portion 2 is delimited by the front transverse edge 27 of the article 1. Furthermore, the front portion 2 extends a certain length b1 along the article 1 in the longitudinal direction. In a sanitary napkin of the type shown, the front portion 2 has a length b1 in the longitudinal direction which is between 10-50%, more preferably between 10-40%, most preferably between 15-25% of the total length b of the article 1. The length can be, for example, between 30-70 mm, such as between 40-60 mm.

The crotch portion 3 of the article 1 is located adjacent to the front portion 2 in the longitudinal direction. In use, the crotch portion 3 lies between the legs of the user and covers a female user's genital region. In a sanitary napkin of the type shown, the crotch portion 3 has a length b2 in the longitudinal direction which is between 25-60%, more preferably between 30-55%, most preferably between 30-50% of the total length b of the article. Typically, the length b2 of the crotch portion 3 in the longitudinal direction y is between 60-150 mm, such as between 80-120 mm.

The rear portion 4 is located at the opposite end of the article 1 from the front portion 2 and is located adjacent to the crotch portion 3 in the longitudinal direction. In use, the rear portion 4 extends towards the user's rear. The rear portion 4 is defined by the rear transverse edge 47 of the article 1 and extends a certain length b3 along the article 1 in the longitudinal direction, and is longitudinally distanced from a centre region 25 of an absorbent core 6. In a sanitary napkin of the type shown, the rear portion 4 has a length b3 in the longitudinal direction which is between 15-40%, more preferably between 20-35%, most preferably between 20-30% of the total length b of the article 1. The length b3 can be, for example, from 60 to 100 mm, such as between 70-90 mm. The length b3 in the rear portion 4 of the article can be extended.

The disposable hygiene article of the present disclosure comprises an absorbent core, which is indicated in the figures with reference sign 6. The "absorbent core" is the absorbent structure of the article which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc., possesses a higher cross-link density than the inner portion of the superabsorbent. The superabsorbent materials may be in any form suitable for use in absorbent composites including particles, fibres, flakes, spheres, and the like. A high absorption capacity is provided by the use of high amounts of superabsorbent material. Thin absorbent cores which are common in, for example, sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as sanitary napkins for adult incontinent persons or panty liners.

Generally, the core can be of unitary construction, whereby, for example, the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition. Likewise, variations in the density or concentration of various components across the longitudinal direction, the transverse direction or the thickness direction of the absorbent core are acceptable, yet the core should not comprise areas or layers of different composition which are formed separately and later joined together.

As shown in FIG. 3, an outer contour of the absorbent core 6 is defined by mirror-image first and second core edge lines 8, 9. The absorbent core 6 is delimited in the front portion 2 by a core front edge 7 and a core rear edge 57 in the rear portion 4. The outer contour defined by the core side edges differs in each of the front, crotch and rear portions 2, 3 and 4.

In FIG. 3, the backsheet is assigned reference numeral 31, the topsheet numeral 30, and the (optional) liquid acquisition layer numeral 36. The absorbent core is assigned reference numeral 6. Suitable materials for the backsheet 31, topsheet 30, and the absorbent core 6 will be apparent to the person skilled in the art.

The acquisition layer 36 can have different shapes, and can be adapted to suit the shape of the absorbent core. In various embodiments, the acquisition layer 36 extends 1-2 mm beyond the outer edge of the core 6 (preferably around the entire periphery of the core 6 according to one embodiment). This configuration can provide neat edges at the periphery of the article.

The absorbent core 6 comprises a first region 12, which is designed and arranged such that it is symmetric about the longitudinal centre line A of the article 1. This is important so that the article 1 lies symmetrically on the user's body when in use. The first region 12 may have the same outer contour as the absorbent core 6, as shown in FIG. 1. In each of the embodiment shown in plan view in FIGS. 1, 2 and 4-7, the outer edge of the core 6 is the same as the outer edge of the first region 12. However, in alternative embodiments (and as will be described in more detail with reference to FIGS. 4A and 4B), the core 6 may have a larger extension in both the transverse x and longitudinal y extension than the first region 12.

The first region 12 comprises in the front portion 2 a head portion 13 and two leg portions 15, 16 extending symmetrically about a centre line A and in a longitudinal direction y of the article 1, starting from a leg portion start point $a_0$ in the crotch portion 3 and extending over a portion of the crotch portion 3 towards separate leg portion endings 17, 18 in the rear portion 4. The outer contour of the head portion 13 is defined by two mirror-imaged substantially convex lines in respect to the longitudinal centre line A. The convex lines converge towards the core rear edge 57 and the first region rear edge 37 so as to define a "neck" for the first region 12, i.e., so as to define the narrowest width M in the transverse direction x for the first portion 12 between first and second first region edge lines 22, 23. The narrowest width M may be at the location of a transition 5, which is an area located between the front portion 2 and the crotch portion 3. Alternatively, the narrowest width M is located in the front portion 2 and the transition 5 is located in the longitudinal direction between the narrowest width M and a transversal line crossing the start point $a_0$ for leg portions 15 and 16 of the core.

As shown in the drawings, the absorbent core 6 further comprises a second region 24. The leg portions 15 and 16 have facing sides 19, 20, which together with a first region rear edge 37 define an outer contour for the second region 24 of the core 6. The second region 24 comprises a centre region 25 and a rear section 38. The portions of the facing sides that oppose each other in the rear section 38 are denoted with reference numerals 19' and 20' in FIG. 3. There is a distance $a_x$ between the facing sides 19, 20 of the respective leg portions 15, 16 in the transverse direction x. The distance $a_x$ varies in the longitudinal direction y. A maximum distance $a_1$ between the facing sides 19, 20 of the respective leg portions 15, 16 in the transverse direction x is in the crotch portion 3. The maximum distance is suitably located at a position in the longitudinal direction y corresponding to a position of a crotch point 21.

The "crotch point" is defined as a middle point of the centre region 25, which is located in a wetting area centrally in the crotch portion 3 of the article. The wetting area is the area where the liquid is initially expected to hit the article. In connection with articles adapted to absorb blood, such as sanitary napkins, it has been found that the crotch point should be located at the point being in contact with introitus. A longitudinal distance between a transversal line at the transition 5, which can correspond to a line drawn between two points at opposite edges 22, 23 of the first region 12 of the core 6 at the point where the first region 12 has its narrowest width M, and the crotch point is about 63 mm when the user is sitting and about 67 mm when the user is standing, whereby an average distance of 65 mm can be calculated. This distance is indicated by reference sign $d_{CP}$ in FIG. 3. The wetting area can then be defined as an area extending symmetrically from the crotch point 21 towards the edges of the article 1. For example, in case of a sanitary napkin, the wetting area includes the centre region 25 and extends from the crotch point 21 longitudinally about 3-4 cm towards the core front edge 7 and/or the core rear edge 57, respectively. Transversally, the wetting area may extend from side edge 8 to side edge 9 of the core 6, but may be narrower. For example, the wetting area may have an extension that substantially corresponds to the extension of the centre region 25. By providing a maximum width, i.e., a maximum distance between the leg portions 15, 16, of the centre region 25 at the point of the crotch point 21, improved liquid control in the wetting area can be provided.

The facing sides 19, 20 of the respective leg portions 15, 16 converge backwards in the longitudinal direction y such that said distance $a_x$ is reduced from the maximum distance $a_1$ to a minimum distance $a_2$ between the rear parts 19', 20' of the facing sides.

The second region 24 is at least partially surrounded by the first region 12 and extends between the leg portions 15, 16 in the transverse direction x and in the longitudinal direction y from the leg portion start point $a_0$ in the crotch portion 3 to a longitudinal endpoint $a_1$ defining the extension of the leg portions 15, 16 in the rear portion 4. The leg portion start point $a_0$ is located in the centre line A so that a symmetrical leg shape can be provided in each longitudinal portion I and II. A distance $a_x$ between facing sides 19, 20 of the respective leg portions 15, 16 in the transverse direction x varies in the longitudinal direction y. In this way portions having different extensions in the transverse direction are provided to improve the fit and the absorbent properties in the article. The facing sides 19, 20 of the respective leg portions 15, 16 converge backwards towards the article rear edge 47 of the article in the longitudinal direction y such that said distance $a_x$ is reduced from said maximum distance $a_1$ to a minimum distance $a_2$. The minimum distance is preferably located outside the wetting area located in the crotch portion and is located in the rear portion 4 of the article 1.

The centre region 25 of the second region 24 is located in the crotch portion 3, and a rear section 38 located in the rear portion 4 of the article 1. The second region 24 is surrounded by the first region 12, except in the first region rear edge 37 area of the core 6. The second region 24 suitably covers from 10-50%, such as from 20-40% of a total area of the core 6. The length of the second region 24 extending along the centre line A between the leg start point $a_0$ an endpoint $a_1$ in the rear portion 4 may vary greatly depending on the size of the article, but can be, for example, from 80 to 220 mm. The rear section 38 may have a length varying from for example 30-110 mm. The centre region 25 may have a length varying from, for example, 50-110 mm. The rear section 38 has a narrower width or extension in the transverse direction x than the centre region 25 or at least a portion of the centre region 25. The rear section 38 can have a lower average density of absorbent material than the centre region 25. Also, the article in the rear section 38 has a lower stiffness than in the first region 12. Alternatively, the centre region 25 and the rear section 38 have substantially the same density. Thus, also the stiffness of the centre region 25 and the rear section 38 may be substantially the same.

The second region 24 which comprises the centre region 25 extending symmetrically about the centre line A, has a longer extension in the longitudinal direction y than in the transverse direction x. Suitably, the centre region has an oval shape or a shape of a parallelogram with edges being located along the centre line A and thus the centre region 25 extends longitudinally and symmetrically about the centre line A. The second region 24 further comprises a longitudinally and symmetrically about the centre line A extending rear section 38. The rear section 38 is in contact with the centre region 25 and can overlap with the centre region 25. Further, the rear section 38 is limited by the facing sides 19, 20 of the respective leg portions 15, 16 and the first region rear edge 37. The facing sides 19', 20' adjacent the rear section 38 can be curved (as shown in FIG. 3) and they can be straight and extend generally parallel to each other.

Generally, the absorbent core 6 has an asymmetrical shape in the longitudinal extension y, but the first and second longitudinal portions I, II are symmetrical in the transverse extension x about the centre line A. The core 6 may have different shapes, but the circumferential edges 8, 9 of the core 6 define a shape in which a head portion 13 and at least one neck area, i.e., an area with smaller width in the transverse direction x, is located in the front portion 2 or in the transition area 5 of the core 6. In this way, the article 1 can better conform to the body shape in the area where the front portion 2 transitions to the crotch portion 3. Practically this means, i.e., that the article 1 can bend in a transversal direction more easily in the area of the neck portion. Therefore, the front portion 2 and the core head portion 13 can bend towards the user and thus the front portion can better cover the pubic regions of the wearer while the crotch portion 3 is able to locate close to the genital area of a female wearer. Also, the article 1 will better be held in its position during the use. The neck area of the core 6 may be the same where the first region 12 of the core 6 has its narrowest width or it may be distanced from that.

The absorbent article 1 according to the present disclosure may further include a liquid acquisition sheet 36, which acts as a liquid distribution layer. The liquid acquisition sheet 36 is located between the topsheet 30 and the core 6 and is suitably placed on top of the absorbent core 6. The liquid acquisition sheet 36 is adapted to quickly receive and temporarily store discharged liquid before it is absorbed by the absorbent core 6. Such acquisition distribution layers may be composed of, for example, airlaid nonwoven, spunlace nonwoven, high loft nonwoven or foam materials. The nonwoven material may be hydrophilic. A hydrophilic material may be obtained by adding a surfactant.

An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The grammage of the airlaid nonwoven can suitably be from 50 to 100 gsm.

A high loft material is a nonwoven material and may be substantially free from absorbing fibres and superabsorbent material. The high loft nonwoven material may comprise thermoplastic polymer fibres, and may be selected from but not limited to, polyesters, polyamides, and polyolefins such as polyethylenes (PE) and polypropylenes (PP) and may be a mixture of any of these. The high loft material refers to low density bulky fabrics, as compared to flat, paper-like fabrics. High loft webs are characterised by a relatively low density. This means that there is a relatively high amount of void space between the fibres. The high loft nonwoven fibrous layer of the present invention may typically have a density below 0.200 g/cc (200 kg/m$^3$), in particular ranging from 0.015 g/cc to 0.150 g/cc (15 kg/m$^3$ to 150 kg/m$^3$), in particular from 0.030 g/cc to 0.100 g/cc (30 to 100 kg/m$^3$), for example 0.065 g/cc (65 kg/m$^3$). The average density can be calculated by dividing the basis weight of the high loft layer by its thickness measured at a pressure of 0.5 kPa (according to the test method referred to in PCT International Application No. PCT/SE2017/050612). Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers. It encompasses 2 processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it, and breaks it up into a fibrous web. The liquid acquisition sheet material may be of a spunbonded material and may be a spunbond-meltbond-spunbond (SMS) material. The high loft nonwoven layer may in particular have a thickness ranging from 0.30 mm to 2.00 mm, for example 1.0 mm as measured at a pressure of 0.5 kPa (according to the test method referred to in PCT International Application No. PCT/SE2017/050612). The grammage, i.e., basis weight of the high loft material may, for example, range from 15 gsm to 500 gsm, in particular from 30 gsm to 200 gsm, such as 30-90 gsm, for example 64 gsm.

According to a further variant, the liquid acquisition sheet 36 is a spunlace, also referred to as spunbond, nonwoven material. A spunlace nonwoven product is derived from a process of entangling a web of loose fibres through multiple rows of jets of water at high pressure; this process entangles the fabrics and interlinks the fibres. There are several terms for spunlace nonwoven fabric or spunlaced, such as jet entangled, needled, hydroentangled or hydraulic, but the term spunlace or spunlaced is the most popular in the nonwoven industry. The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfiber, wherein viscose is the most commonly used raw material. Thus, if a combination of different fibres is used, this can be a mixture of fibres from different polymers, although each fibre can also include different polymers (e.g., PP/PE bi-component fibres or PP/PE copolymers). Where appropriate, the plastic film can consist of PE or PP, PET, PLA, or amyl (or, for that matter, any other thermoplastic polymer), or a mixture or copolymers of the aforementioned polymers. The spunlace material usually comprises polypropylene or polyethylene fibres which provide for optimal comfort for the nonwoven material. Other suitable fibres for making the nonwoven material are, for example, natural fibers such as bamboo, cotton, and flax. The grammage of the spunlace nonwoven material can be typically from 30-80 gsm.

Figure 4A:
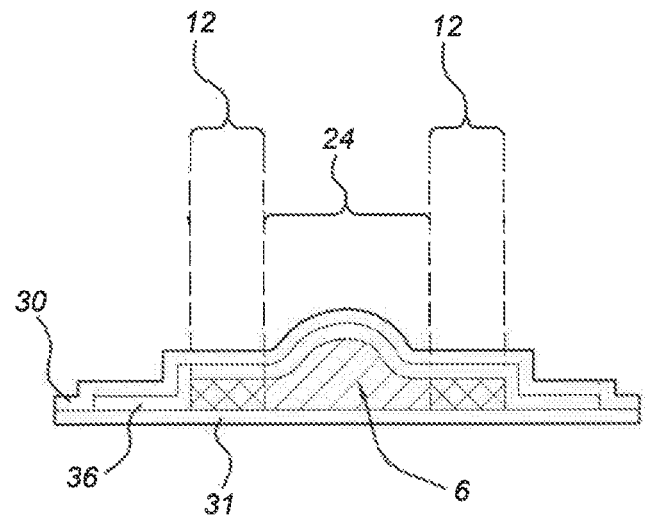
FIG. 4A shows schematically a transverse cross-sectional view an article according to one embodiment of the present disclosure.

FIG. 4A shows a cross-sectional view of the article of FIG. 3, taken along the line B-B. The cross-sectional view of FIG. 4A clearly shows the topsheet 30, the backsheet 31, and the core 6 disposed therebetween. The liquid acquisition sheet is provided between the core 6 and the topsheet 30. In one embodiment, the liquid acquisition sheet 36 has a larger extension in both the transverse x and longitudinal extension y of the core 6 as shown in FIG. 3 and FIG. 4A. In this way it is possible to obtain soft side edge areas. In an exemplary embodiment, the liquid acquisition sheet extends beyond the outer edges of the core 6 by approximately 1-2 mm. This means that the core is completely covered by the liquid acquisition sheet. Leakage control may be improved, especially in the areas where the first region 12 of the core 6 has a narrow extension in the transversal direction x, such as in an area of transition 5 which will be explained more in detail below. Leakage control can be obtained since the liquid acquisition sheet 36 creates a fast inlet to trap the liquid in the product. For example, at least a part of menstrual fluid in the areas outside the core is trapped whereby the fluid will thus not leak outside the hygiene article 1.

Figure 4B:
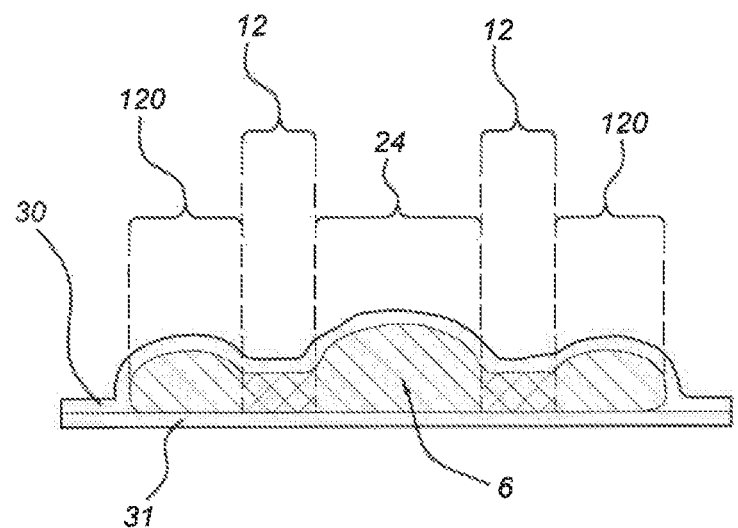
FIG. 4B shows schematically a transverse cross-sectional view of an article according to another embodiment of the present disclosure.

In alternative embodiments, and as shown in FIG. 4B, the liquid acquisition sheet 36 can be omitted. In such embodiments, the article 1 can comprise a topsheet 30, a core 6 and a backsheet 31, as illustrated in FIG. 4B. However, in embodiments in which the acquisition sheet 36 is omitted, it is preferred that the core 6 comprises an outer edge region 120 that surrounds the outer edges of the core 6. The outer edge region 120 of the core 6 can be configured to be less stiff than the first region 12 of the core 6. The outer region 120 of the core 6 can be formed of lower density material or it can have lower compression. In some embodiments, a soft outer core region 120 (that surrounds the first region 12 of the core 6 and is relative soft in comparison thereto) can be combined with a liquid acquisition sheet 36, which extends beyond the outer edges 8, 9 of the core 6.

Referring now to both FIG. 4A and FIG. 4B, the second region 24, and in particular in the centre region 25 is suitably thicker and softer than the first region 12. In both of the embodiments shown in FIGS. 4A and 4B, the centre region 25 provides a pre-formed raised portion, i.e., a preformed raised portion is provided. In addition, due to the fact that the average density of the absorbent core 6 may be lower in the second region 24 than in the first region 12 and the fact that the facing sides 19, 20 of the respective leg portions 15, 16 converge backwards in the longitudinal direction of the article 1, the absorbent article 1 can fold in use along the longitudinal centre line A effectively in at least parts of the crotch portion 3 and the rear portion 4. Thereby, the preformed raised portion in the centre region 25 is further enhanced during use in at least parts of the crotch portion 3. The raised portion is intended to make contact with the genitals of the wearer during use of the article 1. There may also be a raised portion provided in the rear section 38, which has a corresponding thickness as the centre region 25. Alternatively, the rear section 38 may be thinner than the centre region 25. This can be obtained, for example, by providing less absorbent material in the rear section 38 than in the centre region. Discharged bodily fluid can in this way be caught as soon as it leaves the body of the wearer and be absorbed immediately into the article 1 instead of running out over the surface of the latter. The rear section 38 and the optional raised portion are accommodated in the cleft between the user's buttocks. This reduces the leakage from the rear of the article. More specifically, it provides very good protection against leakage via the cleft between the buttocks, which type of leakage usually occurs during the use of conventional absorbent articles when the user is sitting or lying on her back.

As shown in FIG. 4A, the core 6 does not extend to the outer edge of the topsheet and the backsheet. However, the acquisition material 36 extends beyond the outer edges of the core 6 to provide soft edge regions.

As shown in FIG. 4B, the core 6 comprises a soft outer core region 120, which extends around the first region 12 of the core. The outer core region 120 can comprise uncompressed material, or it can comprise material that is compressed to a lesser extent than the first region 12 of the core 6. The material of the outer edge region 120 may be similar to the second region 24 of the core 6. As shown in FIG. 4B, the outer edge regions 120 of the core 6 can therefore have an increased height compared to the first region 12 of the core 6, although this is not essential and soft outer edge regions can be provided without increasing the height of the outer regions 120 compared to the first region 12 of the core 6.

In embodiments comprising an outer core 120, as illustrated in FIG. 4B, the compression lines can extend beyond the outer edge of the first region 12 of the core 6, towards or even to an outer edge of the outer region 120 of the core 6. In such embodiments, the endpoints of the compression lines are adjacent to the outer edge of the first region 12 of the core. Similarly, the compression lines may stop adjacent to the outer edge of the first region 12, just short of the outer edge of the first region 12 of the core 6.

In yet another embodiment (not shown in the drawings, a liquid acquisition material can be provided covering only a portion of the core, for example, a longitudinal central portion of the core. In embodiments in which a liquid acquisition material is provided across over only a portion of the core, the acquisition material may cover at least central region 25. Moreover, in an embodiment in which the liquid acquisition material does not extend beyond an outer edge of the core, the core may comprise a relatively soft outer region 120, as illustrated in FIG. 4B.

Returning now to FIG. 3, in case the article comprises a liquid acquisition sheet 36, the liquid acquisition sheet 36 may comprise a slit extending along the centre line A over at least part of the longitudinal extension of the second region 24. The slit is not depicted in the Figures, however it can extend along the longitudinal centre line A shown in the drawings. It should be noted that the slit can optionally be present in all embodiments of the article according to the present disclosure. By the slit is meant a narrow longitudinally extending cut through, the acquisition layer material. The slit has a width in the transverse direction x that corresponds to an edge of a cutting knife and can be, for example, from 0.05 mm to 1 mm, but the width may be up to about 2 mm. By means of the slit, the second region 24 will be able to bend easily and thus conform to the body shape more effectively. In this way, the second region 24 will be able to rise towards the body of the user when the legs of the user press the side edges of the article. Thus, the slit aids in positioning the product during the use, whereby the secure feeling, leakage control and comfort of the product may be further improved compared to the prior art products on the market.

Although not shown in the drawings, the slit can extend from a start point located in the centre line A in the rear portion 4 between the first region rear edge 37 and the core rear edge 57. The slit can extend up to the leg start point $a_0$ in the crotch portion 3. In one embodiment, the slit does not extend to the front portion 2 of the article 1, since the front portion 2 may bend principally along a transverse bending axis. In this way the front portion 2 will have maximal extension in the transverse direction x and will thus be able to cover the pubic region of the user. By providing the slit so that it extends at least partially along the length of the rear section 38, a certain fold in the rear section is essentially promoted and the comfort of the hygiene article is improved. Therefore, also undesired twisting, bunching or folding of the article between the buttocks is reduced. Folding of the rear section 38 in a controlled way by means of the slit between the user's buttocks also promotes secure fit, as transverse and longitudinal movement of the article during wear is reduced. The different densities in the first region 12 and at least a portion of the second region 24 and the optional slit in the acquisition layer (where present) cooperate in order to provide the article 1 with a form that follows the contours of the wearer's body even more closely. More specifically, the article 1 is provided with a form that molds towards labia during use. The side areas, i.e., outer edge regions of the article 1 comprising the acquisition layer 36 can provide soft edges to the article which increases comfort. Alternatively, as described above, an outer core region can be provided, which surrounds the first region 12 of the core 6, to provide the article with soft edges.

Furthermore, referring still to FIG. 3, since the width M of the first region 12 essentially corresponds to the distance between the two mentioned muscle tendons on the wearer and in that the two side edges 22, 23 of the head part 13 of the first region 12 diverge forwards in the longitudinal direction from the point of narrowest width M, the absorbent article 1 can during use be anchored firmly with the point of narrowest width M or transition 5 between the muscle tendons and be retained in this position. The front portion 2 of the article 1 is therefore held in the area in front of the mentioned muscle tendons, while the crotch portion 3 of the article 1 is effectively positioned correctly against the genitals of the wearer thanks to the slit 39 in the second region 24 enabling the core material underneath the liquid acquisition sheet in the centre region 25 to bulge upwards towards the body of the user when the legs of the user press the article from the sides, whereby a better fit and thus comfort can be obtained on the side of the article facing the body of the user. This helps to avoid problems associated with incorrect placement of the absorbent article 1, or movement of the article 1 during wear. In this way, the article 1 is prevented from moving backwards between the legs of the wearer. Even though a sanitary towel is fastened to the underwear in use, this is a common problem in conventional sanitary towels because the leg movements of the wearer often shift the sanitary towel backwards.

In addition, the higher average density of the first region 12 implies that it has great liquid-spreading capacity for rapid spreading of bodily fluid received from the wearer over the core 6. The higher average density of the first region 12 in the head part 13 also promotes stability, i.e., it promotes that the head part 13 remains out-stretched and that wrinkle formation is inhibited.

A suitable technique for manufacturing the absorbent cores of the present disclosure is mat-forming through an air-laying process. In the process, an air-permeable mould is provided. Fibrous material is air-laid into the mould and the mould is filled, whereby an absorbent core is produced in with a desired amount of fibrous material.

After the absorbent core 6 is produced, it can be pattern-compressed so that an absorbent core having regions with different densities is produced. Compressing may take place using any known means. The average density of the fibrous material in the low-compressed or non-compressed absorbent core corresponds to the average density of the absorbent core in the regions of lower average density, i.e., the second region 24. The absorbent core outside these regions, i.e., in the first region 12, is then compressed while within these regions, the core remains uncompressed.

Thus, the first region of the core is compressed more than the second region. Alternatively, or additionally the first region is embossed to solely provide the higher compression or to further increase compression grade obtained by compression. If the compression and embossing are separate steps, the step of embossing of an embossing pattern can be performed simultaneously or subsequently with the compression to areas providing the first region. The embossing pattern is suitably visible through the top sheet. The compression and embossing can be performed through the topsheet or the backsheet side of the core.

Turning now to FIG. 5, in at least some exemplary embodiments, the first L1, R1 and second L2, R2 pairs of rear compression lines can comprise a first pair of straight compression lines and a second pair of curved compression lines. As shown in FIG. 5, the first pair of compression lines L1, R1 comprise straight compression lines, similar to the compression lines described with reference to FIGS. 1 and 2. However, in the embodiment depicted in FIG. 5, the second pair of compression lines L2, R2 comprise curved lines, that curve away from each other as they extend in the forward direction, from the rear endpoints $PR_{L2,R2}$ to the forward endpoints $PF_{L2, R2}$. The first and second pairs of compression lines shown in FIG. 5 can provide the preferred controlled folding of the article 1 in the region of the perineum and the buttocks, as described above with reference to FIGS. 1 and 2. As an additional advantage, the curved compression lines L2, R2 shown in FIG. 5 may provide improved control and more reliable bending of the article (to conform to the body of the user) by allowing the article to bend along curved lines that approximate the curves of the user's body. The smooth curve of the curved compression lines may allow for improved distribution of force along the compression lines.

As shown in FIG. 5, the curves compression lines L2, R2 may approach the inner edges 19, 20 of the first and second leg portions 15, 16 in the rear portion 4 of the article 1 asymptotically or they may be configured such that the inner edges 19', 20' of the first and second leg portions 15, 16 form a tangential extension of the curved compression lines. Such as arrangement provides a smooth transition between the second pair of compression lines L2, R2 and the edges 19', 20' of the leg portions. This may enhance the ability of the article 1 to adopt a shape in which the rear region 38 of the second region 24 (see FIG. 3) is able to form a ridge to conform to the crease between the user's buttocks.

To provide a smooth transition between the second pair of compression lines L2, R2 and the inner rear edges 19', 20' of the leg portion 15, 16, in embodiments comprising one straight pair of compression lines and one curved pair of compression lines, it is preferred that the second pair of compression lines (towards the rear of the article 1) are curved. However, the skilled person will appreciate that advantages associated with the present invention may also be realized in embodiments in which the each of the first pair of compression lines is curved, and each of the second pair of compression lines is straight.

Figure 6:
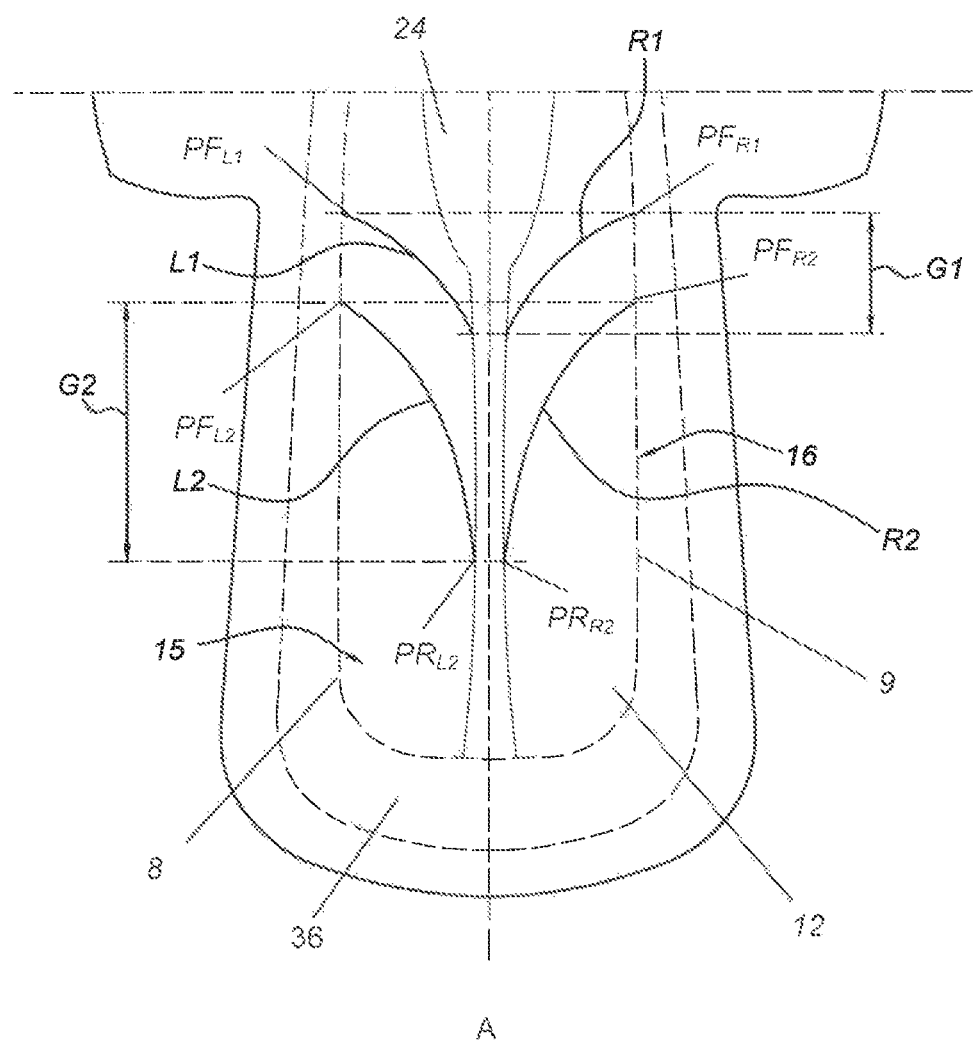
FIG. 6 shows schematically a plan view of a rear portion of an article according to a third embodiment of the disclosure.

As shown in FIG. 6, the article 1 can comprise two pairs of curved compression lines. As shown in FIG. 6, each of the first L1, R1 and second L2, R2 pairs of rear compression lines can comprise compression lines that curve away from each other (and with each curve having its convex side facing the centre line A) as they extend in the forward direction. The curved compression lines L1, R1 of the first pair of compression lines can comprise a radius of curvature that is larger than the radius of curvature of the curved compression lines L2, R2 of the second radius of curvature. As shown in FIG. 6, the distance G2 is larger than the distance G1, providing first and second compression lines that are better able to conform to the user's body in the region of the perineum and the buttocks than known articles.

In embodiments of the present invention comprising first and second pairs of curved compression lines, the compression lines can be substantially parallel, that is a distance between the two curved left compression lines L1, L2, measured in a direction normal to the curve at any given point, remains constant along the length of the curve. In other embodiments, the left compression lines may be non-parallel with respect to each other (similarly for the right compression lines). Since the right compression lines R1, R2 are symmetrical about centre line A to the left compression lines L1, L2, the same can be said of the right compression lines R1, R2.

As shown in FIG. 7, the first and second pairs of compression lines L1, R1, L2, R2 described in connection with FIGS. 1 to 6 can be combined with additional front compression lines 101, 102 in the front 2 and/or crotch 3 region of the article 1. The additional front compression lines 101, 102 can be provided to improve the fit of the article in the front region of the article, i.e., in the pubic region of the user. The combination of the rear compression lines described above and the front compression lines illustrated in FIG. 7 is that the fit of the article in the forward direction and the rearward direction can be improved. Such an improved fit can allow the central region 25 of the article to be maintained in close contact with the user's body at the wetting point, which can improve liquid capture and storage. Moreover, by controlling the bending article 1 in the front 2 and rear 4 portions, security against leakage is improved, because bending and creasing of the article 1 can be controlled in a manner that does not form (or forms to a lesser extent) channels along which fluid can escape from the article 1.

As shown in FIG. 7, the front compression lines 101, 102 can comprise separate first and second front compression lines. The first compression line 101 can extend from a front endpoint $PF_1$ to a rear endpoint $PR_1$ via a first turning point $T_1$. The second compression line 102 extends from a front endpoint $PF_2$ to a rear endpoint $PR_2$ via a second turning point $T_2$.

As shown in FIG. 7, the front endpoint $PF_1$ of the first (left) front compression line 101 is located at or adjacent to an outer edge 8 of the first region 12 of the core, left of the longitudinal centre line A and forward of the narrowest width M. The rear endpoint $PR_1$ of the left front compression line 101 is located at or adjacent to an outer edge 8 of the first region 12 of the core 6, left of the centre line A and rearward of the narrowest width M. The first turning point $T_1$ is located left of the centre line A, right of the front and rear endpoints $PF_1$, $PR_1$, and between the front and rear endpoints in the longitudinal direction. Therefore, the left front compression line 101 extends from a point at or adjacent to an outer edge of the first region 12 towards the centre line A, before turning at turning point T1 and extending away from the centre line A and back toward the outer edge 8 of the first region 12 of the core 6. The left front compression line 101 therefore extends only in the left-hand portion I of the article 1, left of the centre line A, and does not cross or meet the centre line A.

The second (right) front compression line 102 is configured as a mirror image of the left front compression line 101, as shown in FIG. 7. Therefore, the front endpoint $PF_2$ of the right front compression line 102 is located at an or adjacent to an outer edge 9 of the first region 12 of the absorbent core 6, right of the longitudinal centre line A and forward of the narrowest width M. The rear endpoint $PR_2$ of the right front compression line 102 is located at or adjacent to an outer edge of the first region 12 of the absorbent core 6 right of the centre line A and behind the narrowest portion M, and the second turning point $T_2$ is located right of the centre line A and left of the front and rear endpoints in the transverse direction, and between the front and rear endpoints in the longitudinal direction y.

As shown in FIG. 7, the left and right front compression lines 101, 102 can be spaced apart from each other at their closest point by a minimum distance D1, between their respective turning points T1, T2. The minimum distance D1 between the left and right front compression lines 101, 102 provides a separation or gap between the lines 101, 102 in which the material of the core is not compressed (or is compressed to a lesser extent that the remainder of the core). The gap between the front compression lines 101, 102 ensures that flow of fluid in the forward direction is allowed in a controlled manner, without the flow being impeded by a compression line extending across the entire width of the first region 12 of the core 6. Moreover, by providing a space between the compression lines 101, 102, potential weak spots created by overlapping compression lines are avoided.

The minimum distance D1 can be at least 1 mm, more preferably at least 2 mm and, more preferably at least 3 mm. In preferred embodiments, the minimum distance D1 is less than 20 mm, more preferably less than 10 mm.

By providing compression lines along which the article can fold or deform when compressed, the position of the folds and creases can be controlled in such a manner that the risk of leakage is minimized. However, the position of compression lines should be carefully considered to avoid that other properties of the article are not unduly compromised. For example, the compression lines should not weaken the structure of the article to such a degree that it becomes prone to tearing. Moreover, the compression lines should not impede the distribution of fluid throughout the article in such a manner that increases the likelihood of leaks.

In addition to the front compression lines shown in FIG. 7, alternative front compression lines can also be combined with the rear compression lines of the present disclosure. For example, front compression lines as shown and described in PCT International Application No. PCT/SE2017/050610 can also be incorporated in combination with rear compression lines described herein. The disclosure of PCT International Application No. PCT/SE2017/050610 is incorporated by reference in its entirety and its contents may be combined with the embodiment described herein to provide additional benefits in connection with the present invention.

The rear compression lines L1, R1, L1, L2 (and any additional compression lines) described herein may be provided by means of groove or line compressing the core 6 and optionally a liquid acquisition sheet and/or topsheet with high pressure compression from the topsheet or backsheet side of the article. The backsheet of the article can be retained unacted and the liquid impermeability of the backsheet is not affected and can be maintained. Methods of manufacturing the above described article according to such means are intended to fall within the scope of the present invention.

Figure 8:
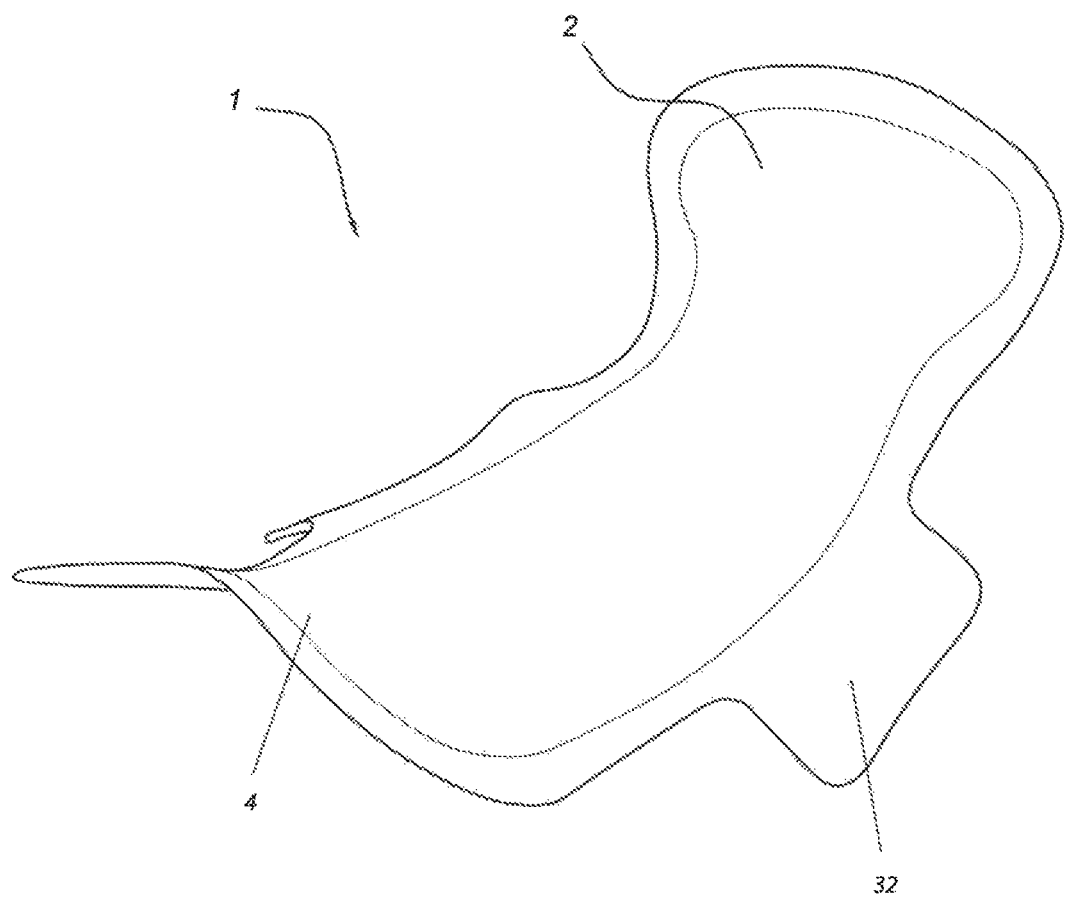
FIG. 8 shows schematically the bending of an article during use.

FIG. 8 shows schematically how articles according to the present invention are adapted to conform to the anatomy of the user. As shown in FIG. 8, the features described with reference to the preceding figures facilitate folding and/or deformation of the article 1 in a manner that better conforms to the anatomy of the user, thereby increasing comfort and preventing leaks. As shown, the rear region 4 of the article is configured to curve upwardly to follow the curve of the user's body in the pubic area.

As illustrated in FIG. 8 (and shown in more detail in FIG. 3) the topsheet 30 and the backsheet 31 and the acquisition sheet 36 each may extend with edge portions outside the absorbent core 6 around the core. The topsheet 30 and the backsheet 31 and optionally the acquisition sheet 36 may be interconnected along edge portions to form a cover around the absorbent core 6. The acquisition sheet 36 may have a smaller extension than the topsheet 30 and the backsheet 1. Suitably, at least the topsheet 30 and the backsheet 31 have substantially the same extension. The cover formed by the topsheet 30 and the backsheet 31 may extend outwards in the transverse direction to form flexible side flaps 32 or "wings", in the region of the crotch portion 3. The side flaps 32 are intended to be arranged around the crotch portion on the briefs of the wearer. Furthermore, the side flaps 32 are suitably provided with adhesive coating (not shown) on the backsheet 31, by means of which the wings 32 can be attached around the crotch portion on the briefs.

However, although all exemplary embodiments illustrated in the drawing comprise wings 32, the skilled person will appreciate that this is not essential to the definition of the present invention, and that the absorbent article 1 may be provided in variants that do not comprise any wings.

Furthermore, in an alternative embodiment, the absorbent article 1 may only comprise a backsheet 31, i.e., no topsheet. Additionally, the absorbent core 6 of the absorbent article may be wrapped in a single coversheet which can act as both inner and backsheet.

The absorbent article 1 defined above may comprise any attachment means known in the art to allow fastening to undergarments of a wearer. Such means may include a coating of adhesive or friction coating on the garment-facing surface of the article. Furthermore, the article 1 according to the present invention may comprise, as above described, attachment flaps ("wings") which extend in the transverse direction of the article 1 and are intended to be arranged around the crotch portion on the briefs of the wearer. It is however important that the nature and placement of such attachment means does not significantly interfere with the function of the article 1 in use.

Although the above description has been exemplified through a sanitary napkin, the present invention is also applicable to other absorbent articles such as diapers, incontinence pads or panty-liners. For instance, application of the present invention to diapers would provide similar benefits in terms of comfort, fit and leakage-prevention.

The present invention should not be considered as limited by the above description; rather the scope and limitations of the present invention are defined by the enclosed claims.

What is claimed is:

1. A disposable hygiene article comprising a transverse direction (x), a longitudinal direction (y) and a longitudinal centre line (A) dividing the article into left-hand and right-hand portions (I) and (II), whereby said article has a front portion, a crotch portion and a rear portion, and said article comprises a liquid-permeable topsheet, a liquid-impermeable backsheet, an absorbent core arranged between the topsheet and backsheet, wherein an outer contour of the absorbent core is defined by mutually symmetrical mirror-imaged portions arranged symmetrically about the centerline (A), and defined by first and second core edge lines, and the core is delimited by a core front edge in the front portion and a core rear edge in the rear portion, whereby said absorbent core comprises a first region extending in the longitudinal direction (y) of the article from a first region front edge in the front portion over the crotch portion to the rear portion, and wherein the outer contour of the first region is defined by mirror-imaged first and second first region edge lines, and whereby said first region comprises a head part and two leg portions extending symmetrically about the centre line (A) and in a longitudinal direction (y) of the article, starting and diverging from a common leg portion start point ($a_0$) in the crotch portion and extending over a portion of the crotch portion towards separate leg portion endings in the rear portion, whereby a distance ($a_x$) between facing sides of the respective leg portions in the transverse direction (x) varies in the longitudinal direction (y), whereby a maximum distance ($a_1$) between the facing sides of the respective leg portions in the transverse direction (x) is in the crotch portion, located at a position in the longitudinal direction (y) corresponding to a position of a crotch point, whereby said facing sides of the respective leg portions converge backwards in the longitudinal direction (y) such that said distance ($a_x$) is reduced from said maximum distance ($a_1$) to a minimum distance ($a_2$), whereby said absorbent core further comprises a second region at least partially surrounded by said first region and extending between said leg portions in the transverse direction (x) and in the length direction (y) from the leg portion start point ($a_0$) in the crotch portion to an end point ($a_1$) in the rear portion, wherein the second region has an average density which is at least 20% lower than the average density of the first region, the absorbent core further comprising:
a first pair of rear compression lines mutually diverging from each other in a forward direction, and
a second pair of rear compression lines mutually diverging from each other in a forward direction,
wherein the first pair of compression lines comprises a left compression line (L1) left of the longitudinal centre line (A) and a right compression line (R1) right of the longitudinal centre line (A), the first and second compression lines (L1, R1) of the first pair of compression lines being mutually symmetric about the longitudinal centerline (A), wherein the second pair of compression lines comprises a left compression line (L2) left of the longitudinal centre line (A) and a right compression line (R2) right of the longitudinal centre line (A), the first and second compression lines (L2, R2) of the second pair of compression lines being mutually symmetric about the longitudinal centerline (A), wherein the first left compression line (L1) extends from a front endpoint ($PF_{L1}$) located at or adjacent to a transversally outer left edge of the first leg portion to a rear endpoint ($PR_{L1}$) located at or adjacent to an inner right edge of the first leg portion, wherein the second left compression line (L2) extends from a front endpoint ($PF_{L2}$) located at or adjacent to a transversally outer left edge of the first leg portion to a rear endpoint ($PR_{L2}$) located at or adjacent to an inner right edge of the first leg portion, wherein the first right compression line (R1) extends from a front endpoint ($PF_{R1}$) located at or adjacent to a transversally outer right edge of the second leg portion to a rear endpoint ($PR_{R1}$) located at or adjacent an inner left edge of the second leg portion, wherein the second right compression line (R2) extends from a front endpoint ($PF_{R2}$) located at or adjacent to a transversally outer left edge of the second leg portion to a rear endpoint ($PR_{R2}$) located at or adjacent to an inner left edge of the second leg portion, wherein the first pair of rear compression lines (L1, R1) is positioned longitudinally forward of the second pair of rear compression lines (L2, R2);

wherein the front endpoint ($PF_{L1}$, $PF_{R1}$) and the rear endpoint ($PR_{L1}$, $PR_{R1}$) of each of the first pair of compression lines (L1, R1) are spaced from each other in a longitudinal direction (y) by a first longitudinal distance G1, wherein the front endpoint ($PF_{L2}$, $PF_{R2}$) and the rear endpoint ($PR_{L2}$, $PR_{R2}$) of each of the second pair of compression lines (L2, R2) are spaced from each other in a longitudinal direction (y) by a second longitudinal distance G2, wherein G2 is larger than G1, and wherein a boundary is defined between the first region and the second region of the core between the first and second leg portions, to form:
a first boundary line between an inner edge of the first leg and the second region; and
a second boundary line between an inner edge of the second leg and the second region, and
wherein the at least one of the first and second pairs of compression lines is curved, and wherein the first boundary line forms a tangential extension of the left curved compression line(s) (L1, L2) at the respective rear endpoint, and wherein the second boundary line forms a tangential extension of the right curved compression line(s) (R1, R2) at the respective rear end point.

2. A disposable hygiene article according to claim 1, wherein the front endpoints of the second pair of rear compression lines (L2, R2) are located longitudinally forward of the rear end points of the first pair of rear compression lines (L1, R1).

3. A disposable hygiene article according to claim 1, wherein the front endpoints ($PF_{L1}$, $PF_{R1}$) of the first pair of rear compression lines (L1, R1) are located longitudinally forward of the front endpoints ($PF_{L2}$, $PF_{R2}$) of the second pair of rear compression lines (L2, R2).

4. A disposable hygiene article according to claim 1, wherein a distance G3 is defined in the transverse direction (x) between opposing mirror image-points on the first pair of compression lines (L1, R1), and wherein the distance G3 increases from a minimum distance $G3_{min}$ between the rear endpoints of the first pair compression lines (L1, R1), and increases continuously in a forward direction to a maximum distance $G3_{max}$ between the front endpoints of the first pair of compression lines (L1, R1).

5. A disposable hygiene article according to claim 4, wherein the first and second left compression lines (L1, L2) and the first and second right compression lines (R1, R2) are curved and curve outwards away from the centre line (A) in the forward direction.

6. A disposable hygiene article according to claim 4, wherein the first pair of rear compression lines and the second pair of rear compression lines are curved, and wherein the left compression lines of the first and second pairs of compression lines are substantially parallel to each other and wherein the right compression lines (R1, R2) of the first and second pairs of compression lines are substantially parallel to each other.

7. A disposable hygiene article according to claim 4, wherein the first pair of rear compression lines (L1, R1) is straight, and the second pair of rear compression lines (L2, R2) curve outwards away from the longitudinal centre line.

8. A disposable hygiene article according to claim 1, wherein a distance G4 is defined in the transverse direction (x) between opposing mirror-image points on the second pair of compression lines (L2, R2), and wherein the G4 increases from a minimum distance $G4_{min}$ between the rear endpoints of the second pair of compression lines (L2, R2) to a maximum distance $G4_{max}$ between front endpoints of the second pair of compression lines (L2, R2).

9. A disposable hygiene article according to claim 1, wherein the first and second compression lines of the first pair of compression lines (L1, R1) and the first and second compression lines of the second pair of compression lines (L2, R2) are straight.

10. A disposable hygiene article according to claim 1, wherein the left and right compression lines one of the first and second pairs of rear compression lines comprises curved lines that curve outwards away from the centre line (A) in a forward direction, and wherein the other of the first and second pairs of compression lines comprises straight lines.

11. A disposable hygiene article according to claim 1, wherein the first region has its narrowest width (M) in the transverse direction (x) in the front portion or at the location of a transition between the front portion and the crotch portion.

12. A disposable hygiene article according to claim 1, wherein the left and right compression lines of each pair of compression lines are continuously and increasingly divergent from each other as they extend in the forward direction.

13. A disposable hygiene article according to claim 1, wherein the first and second rear compression lines are obtained by means of groove compressing the core and optionally the acquisition sheet and/or the topsheet with high pressure compression from the topsheet.

14. A disposable hygiene article according to claim 1, wherein the second region comprises a centre region extending symmetrically about the centre line (A) and having a longer extension in the longitudinal direction (y) than in the transverse direction (x), and a longitudinally and symmetrically about the centre line (A) extending rear section in contact with the centre region, and the centre region and the rear section being limited by the facing sides of the respective leg portions.

15. A disposable hygiene article according to claim 14, wherein a maximum width ($a_1$) of the centre region is 10-50 mm and a length is from 50-110 mm, and the minimum width ($a_2$) of a rear section limited by the facing sides of the respective leg portions is 5-30 mm and a length is from 30-110 mm.

16. A disposable hygiene article according to claim 14, wherein the centre region extends in a thickness direction (D) of the article such that it protrudes outwards from a plane of the first region.

17. A disposable hygiene article according to claim 1, wherein the first region has an average density of an absorbent material from 150-220 kg/m$^3$, and the second region has an average density of an absorbent material from 70-150 kg/m$^3$.

18. A disposable hygiene article according to claim 1, wherein the higher average density of the absorbent material is obtained by means of compression and/or providing an embossing pattern to the first region which covers at least portion of the first region, and wherein the second region is free of the embossing pattern.

19. A disposable hygiene article according to claim 18, wherein said first region is compressed more than the second region, and the first region is stiffer than the second region.

20. The disposable hygiene article of claim 18, wherein the embossing pattern comprises individual dots placed in a predetermined pattern.

21. A disposable hygiene article according to claim 1, wherein the second region covers from 10-50% of a total area of the core.

22. A disposable hygiene article according to claim 1, wherein G2 is [at least 5% longer] than G1.

23. A disposable hygiene article according to claim 1, wherein the first pair of compression lines is configured to allow the hygiene article to conform to a curvature of a user's body in the region of the perineum, and
  wherein the second pair of compression lines is configured to allow the hygiene article to form a longitudinal ridge in a rear portion of the article to conform to the user's body in between the buttocks.

24. A disposable hygiene article comprising a transverse direction (x), a longitudinal direction (y) and a longitudinal centre line (A) dividing the article into left-hand and right-hand portions (I) and (II), whereby said article has a front portion, a crotch portion and a rear portion, and said article comprises a liquid-permeable topsheet, a liquid-impermeable backsheet, an absorbent core arranged between the topsheet and backsheet, wherein an outer contour of the absorbent core is defined by mutually symmetrical mirror-imaged portions arranged symmetrically about the centerline (A), and defined by first and second core edge lines, and the core is delimited by a core front edge in the front portion and a core rear edge in the rear portion, whereby said absorbent core comprises a first region extending in the longitudinal direction (y) of the article from a first region front edge in the front portion over the crotch portion to the rear portion, and wherein the outer contour of the first region is defined by mirror-imaged first and second first region edge lines, and whereby said first region comprises a head part and two leg portions extending symmetrically about the centre line (A) and in a longitudinal direction (y) of the article, starting and diverging from a common leg portion start point ($a_0$) in the crotch portion and extending over a portion of the crotch portion towards separate leg portion endings in the rear portion, whereby a distance ($a_x$) between facing sides of the respective leg portions in the transverse direction (x) varies in the longitudinal direction (y), whereby a maximum distance ($a_1$) between the facing sides of the respective leg portions in the transverse direction (x) is in the crotch portion, located at a position in the longitudinal direction (y) corresponding to a position of a crotch point, whereby said facing sides of the respective leg portions converge backwards in the longitudinal direction (y) such that said distance ($a_x$) is reduced from said maximum distance ($a_1$) to a minimum distance ($a_2$), whereby said absorbent core further comprises a second region at least partially surrounded by said first region and extending between said leg portions in the transverse direction (x) and in the length direction (y) from the leg portion start point ($a_0$) in the crotch portion to an end point ($a_1$) in the rear portion, wherein the second region has an average density which is at least 20% lower than the average density of the first region,
  the absorbent core further comprising:
    a first pair of rear compression lines mutually diverging from each other in a forward direction, and
    a second pair of rear compression lines mutually diverging from each other in a forward direction,
    wherein the first pair of compression lines comprises a left compression line (L1) left of the longitudinal centre line (A) and a right compression line (R1) right of the longitudinal centre line (A), the first and second compression lines (L1, R1) of the first pair of compression lines being mutually symmetric about the longitudinal centerline (A),
    wherein the second pair of compression lines comprises a left compression line (L2) left of the longitudinal centre line (A) and a right compression line (R2) right of the longitudinal centre line (A), the first and second compression lines (L2, R2) of the second pair of compression lines being mutually symmetric about the longitudinal centerline (A),
    wherein the first left compression line (L1) extends from a front endpoint ($PF_{L1}$) located at or adjacent to a transversally outer left edge of the first leg portion to a rear endpoint ($PR_{L1}$) located at or adjacent to an inner right edge of the first leg portion,
    wherein the second left compression line (L2) extends from a front endpoint ($PF_{L2}$) located at or adjacent to a transversally outer left edge of the first leg portion to a rear endpoint ($PR_{L2}$) located at or adjacent to an inner right edge of the first leg portion,
    wherein the first right compression line (R1) extends from a front endpoint ($PF_{R1}$) located at or adjacent to a transversally outer right edge of the second leg portion to a rear endpoint ($PR_{R1}$) located at or adjacent an inner left edge of the second leg portion,
    wherein the second right compression line (R2) extends from a front endpoint ($PF_{R2}$) located at or adjacent to a transversally outer left edge of the second leg portion to a rear endpoint ($PR_{R2}$) located at or adjacent to an inner left edge of the second leg portion, wherein the first pair of rear compression lines (L1, R1) is positioned longitudinally forward of the second pair of rear compression lines (L2, R2);
    wherein the front endpoint ($PF_{L1}$ $PF_{R1}$) and the rear endpoint ($PR_{L1}$, $PR_{R1}$) of each of the first pair of compression lines (L1, R1) are spaced from each other in a longitudinal direction (y) by a first longitudinal distance G1, wherein the front endpoint ($PF_{L2}$ $PF_{R2}$) and the rear endpoint ($PR_{L2}$ $PR_{R2}$) of each of the second pair of compression lines (L2, R2) are spaced from each other in a longitudinal direction (y) by a second longitudinal distance G2, and wherein G2 is larger than G1, the disposable hygiene article further comprising left and right front compression lines, said left and right compression lines being symmetrically arranged about the centre line (A), wherein the left front compression line extends from a front endpoint to a rear endpoint via a first turning point (T1), and wherein:

the front endpoint of the front left compression line is located at or adjacent to an outer edge region of the first region of the absorbent core left of the longitudinal centre line (A) and forward of a point of narrowest width (M) of the core, the rear endpoint of the front left compression line is located at or adjacent to an outer edge region of the first region of the absorbent core left of the centre line (A) and behind the narrowest width (M), and the first turning point (T1) is located left of the centre line (A) and right of the front and rear endpoints in the transverse direction (x), and between the front and rear end points in the longitudinal direction (y), wherein the right front compression line extends from a front endpoint to a rear endpoint via a second turning point (T2), and wherein:

the front endpoint of the front right compression line is located at or adjacent to an outer edge region of the first region of the absorbent core right of the longitudinal centre line (A) and forward of the narrowest width (M), the rear endpoint of the front right compression line is located at or adjacent to an outer edge region of the first region of the absorbent core right of the centre line (A) and behind the narrowest portion (M), and the second turning point (T2) is located right of the centre line (A) and left of the front and rear endpoints in the transverse direction (x), and between the front and rear end points in the longitudinal direction (y).

25. A disposable hygiene article comprising a transverse direction (x), a longitudinal direction (y) and a longitudinal centre line (A) dividing the article into left-hand and right-hand portions (I) and (II), whereby said article has a front portion, a crotch portion and a rear portion, and said article comprises a liquid-permeable topsheet, a liquid-impermeable backsheet, an absorbent core arranged between the topsheet and backsheet, wherein an outer contour of the absorbent core is defined by mutually symmetrical mirror-imaged portions arranged symmetrically about the centerline (A), and defined by first and second core edge lines, and the core is delimited by a core front edge in the front portion and a core rear edge in the rear portion, whereby said absorbent core comprises a first region extending in the longitudinal direction (y) of the article from a first region front edge in the front portion over the crotch portion to the rear portion, and wherein the outer contour of the first region is defined by mirror-imaged first and second first region edge lines, and whereby said first region comprises a head part and two leg portions extending symmetrically about the centre line (A) and in a longitudinal direction (y) of the article, starting and diverging from a common leg portion start point ($a_0$) in the crotch portion and extending over a portion of the crotch portion towards separate leg portion endings in the rear portion, whereby a distance (ag) between facing sides of the respective leg portions in the transverse direction (x) varies in the longitudinal direction (y), whereby a maximum distance ($a_1$) between the facing sides of the respective leg portions in the transverse direction (x) is in the crotch portion, located at a position in the longitudinal direction (y) corresponding to a position of a crotch point, whereby said facing sides of the respective leg portions converge backwards in the longitudinal direction (y) such that said distance ($a_x$) is reduced from said maximum distance ($a_1$) to a minimum distance ($a_2$), whereby said absorbent core further comprises a second region at least partially surrounded by said first region and extending between said leg portions in the transverse direction (x) and in the length direction (y) from the leg portion start point ($a_0$) in the crotch portion to an end point (a) in the rear portion, wherein the second region has an average density which is at least 20% lower than the average density of the first region, the absorbent core further comprising:

a first pair of rear compression lines mutually diverging from each other in a forward direction, and a second pair of rear compression lines mutually diverging from each other in a forward direction, wherein the first pair of compression lines comprises a left compression line (L1) left of the longitudinal centre line (A) and a right compression line (R1) right of the longitudinal centre line (A), the first and second compression lines (L1, R1) of the first pair of compression lines being mutually symmetric about the longitudinal centerline (A), wherein the second pair of compression lines comprises a left compression line (L2) left of the longitudinal centre line (A) and a right compression line (R2) right of the longitudinal centre line (A), the first and second compression lines (L2, R2) of the second pair of compression lines being mutually symmetric about the longitudinal centerline (A), wherein the first left compression line (L1) extends from a front endpoint ($PF_{L1}$) located at or adjacent to a transversally outer left edge of the first leg portion to a rear endpoint ($PR_{L1}$) located at or adjacent to an inner right edge of the first leg portion, wherein the second left compression line (L2) extends from a front endpoint ($PF_{L2}$) located at or adjacent to a transversally outer left edge of the first leg portion to a rear endpoint ($PR_{L2}$) located at or adjacent to an inner right edge of the first leg portion, wherein the first right compression line (R1) extends from a front endpoint ($PF_{R1}$) located at or adjacent to a transversally outer right edge of the second leg portion to a rear endpoint ($PR_{R1}$) located at or adjacent an inner left edge of the second leg portion, wherein the second right compression line (R2) extends from a front endpoint ($PF_{R2}$) located at or adjacent to a transversally outer left edge of the second leg portion to a rear endpoint ($PR_{R2}$) located at or adjacent to an inner left edge of the second leg portion, wherein the first pair of rear compression lines (L1, R1) is positioned longitudinally forward of the second pair of rear compression lines (L2, R2);

wherein the front endpoint ($PF_{L1}$ $PF_{R1}$) and the rear endpoint ($PR_{L1}$, $PR_{R1}$) of each of the first pair of compression lines (L1, R1) are spaced from each other in a longitudinal direction (y) by a first longitudinal distance G1, wherein the front endpoint ($PF_{L2}$ $PF_{R2}$) and the rear endpoint ($PR_{L2}$ $PR_{R2}$) of each of the second pair of compression lines (L2, R2) are spaced from each other in a longitudinal direction (y) by a second longitudinal distance G2, and wherein G2 is larger than G1, the disposable hygiene article further comprising left and right front compression lines, said left and right compression lines being symmetrically arranged about the centre line (A), wherein the left front compression line extends from a front endpoint to a rear endpoint via a first turning point (T1), and wherein:

the front endpoint of the front left compression line is located at or adjacent to an outer edge region of the first region of the absorbent core left of the longitudinal centre line (A) and forward of a point of narrowest width (M) of the core, the rear endpoint of the front left compression line is located at or adjacent to an outer edge region of the first region of the absorbent core left of the centre line (A) and behind the narrowest width (M), and the first turning point (T1) is located left of the centre line (A) and right of the front and rear endpoints in the transverse direction (x), and between the front and rear end points in the longitudinal direction (y), wherein the right front compression line extends from a front endpoint to a rear endpoint via a second turning point (T2), and wherein:

the front endpoint of the front right compression line is located at or adjacent to an outer edge region of the first region of the absorbent core right of the longitudinal centre line (A) and forward of the narrowest width (M), the rear endpoint of the front right compression line is located at or adjacent to an outer edge region of the first region of the absorbent core right of the centre line (A) and behind the narrowest portion (M), the second turning point (T2) is located right of the centre line (A) and left of the front and rear endpoints in the transverse direction (x), and between the front and rear end points in the longitudinal direction (y), and wherein the left front compression line and the right front compression line are spaced from each other by a minimum distance G7 between their respective turning points (T1, T2), and wherein the distance G7 is at least 1 mm in a transverse direction (x).

26. A method for the manufacture of the disposable hygiene article according to claim 1, comprising the steps of:

feeding a liquid-permeable topsheet material layer, a liquid-impermeable backsheet material layer and an absorbent material layer arranged to be positioned in between the topsheet material layer and the backsheet material layer, forming the first region and second region of the core by compressing the first region more than the second region and/or by embossing an embossing pattern to areas providing the first region in the core, and forming the first pair of rear compression lines (L1, R1) and the second pair of rear compression lines (L2, R2), by means of high pressure compression from the topsheet of the core.

27. The method according to claim 26, wherein the first region is formed prior to marriage of the backsheet to the absorbent core, topsheet and optional liquid acquisition sheet of the article.

28. The method according to claim 26, wherein the method further comprises providing an acquisition material layer between the topsheet material layer and the absorbent material layer.

* * * * *